US010626378B2

(12) United States Patent
Moore et al.

(10) Patent No.: US 10,626,378 B2
(45) Date of Patent: Apr. 21, 2020

(54) RESPIRATORY SYNCYTIAL VIRUS EXPRESSION VECTORS

(71) Applicants: Emory University, Atlanta, GA (US); Children's Healthcare of Atlanta, Inc., Atlanta, GA (US)

(72) Inventors: Martin L. Moore, San Carlos, CA (US); Anne Hotard, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 16/275,650

(22) Filed: Feb. 14, 2019

(65) Prior Publication Data

US 2019/0169579 A1    Jun. 6, 2019

Related U.S. Application Data

(62) Division of application No. 13/444,338, filed on Apr. 11, 2012, now Pat. No. 10,227,569.

(60) Provisional application No. 61/474,365, filed on Apr. 12, 2011.

(51) Int. Cl.
| | |
|---|---|
| *C12N 15/00* | (2006.01) |
| *C12N 15/10* | (2006.01) |
| *C12N 15/63* | (2006.01) |
| *C12P 19/34* | (2006.01) |
| *C12Q 1/68* | (2018.01) |
| *C12N 7/00* | (2006.01) |
| *C12N 15/86* | (2006.01) |

(52) U.S. Cl.
CPC ............. *C12N 7/00* (2013.01); *C12N 15/86* (2013.01); *C12N 2760/18543* (2013.01); *C12N 2760/18552* (2013.01); *C12N 2800/204* (2013.01); *C12N 2800/50* (2013.01)

(58) Field of Classification Search
CPC ............ C12Q 1/6827; C12Q 2521/531; C12Q 2537/164; C12N 15/1034; C12N 15/63
See application file for complete search history.

(56) References Cited

U.S. PATENT DOCUMENTS

| | | | | |
|---|---|---|---|---|
| 5,618,682 | A | 4/1997 | Scheirer | |
| 5,674,713 | A | 10/1997 | McElroy | |
| 5,976,796 | A | 11/1999 | Szalay | |
| 6,074,859 | A | 6/2000 | Hirokawa | |
| 6,790,449 | B2 | 9/2004 | Collins | |
| 6,828,102 | B2 * | 12/2004 | Lowry | C12Q 1/683 435/320.1 |
| 7,572,904 | B2 | 8/2009 | Cheng | |
| 7,892,822 | B1 | 2/2011 | Koszinowski | |
| 10,227,569 | B2 | 3/2019 | Moore | |

OTHER PUBLICATIONS

Adler, et al., (2003), "Cloning of herpesviral genomes as bacterial artificial chromosomes", Reviews in Medical Virology, 13(2): 111-121.
Buchholz, et al., (2000), "Chimeric Bovine Respiratory Syncytial Virus with Glycoprotein Gene Substitutions from Human Respiratory Syncytial Virus (HRSV): Effects on Host Range and Evaluation as a Live-Attenuated HRSV Vaccine.", Journal of Virology, 74(3): 1187-1199.
Clements, et al., (1991), "Evaluation of bovine, cold-adapted human, and wild-type human parainfluenza type 3 viruses in adult volunteers and in chimpanzees.", Journal of Clinical Microbiology, 29(6): 1175-1182.
Collins, et al., (1986), "Nucleotide sequences for the gene junctions of human respiratory syncytial virus reveal distinctive features of intergenic structure and gene order.", Proceedings of the National Academy of Sciences, 83(13): 4594-4598.
Collins, et al., (1987), "Gene overlap and site-specific attenuation of transcription of the viral polymerase L gene of human respiratory syncytial virus.", Proceedings of the National Academy of Sciences, 84(15): 5134-5138.
Collins, et al., (1991) Evaluation of Bovine, Cold-Adapted Human, and Wild-Type Human Parainfluenza Type 3 Viruses in Adult Volunteers and in Chimpanzees, Journal of Clinical Microbiology, 29(6):1175-1182.
Collins, et al., (1995), "Production of infectious human respiratory syncytial virus from cloned cDNA confirms an essential role for the transcription elongation factor from the 5' proximal open reading frame of the M2 mRNA in gene expression and provides a capability for vaccine development.", Proceedings of the National Academy of Sciences, 92(25): 11563-11567.
Cunningham, et al., (1993), "Lentivirus envelope sequences and pro viral genomes are stabilized in *Escherichia coli* when cloned in low-copy-number plasmid vectors.", Gene, 124(1): 93-98.
De Wet, et al., (1987), "Firefly luciferase gene: structure and expression in mammalian cells.", Molecular and Cellular Biology, 7(2): 725-737.
Hotard et al. (2012) A stabilized respiratory syncytial virus reverse genetics system amenable to recombination-mediated mutagenesis, Virology 434:129-136.
Karron, et al., (2005), "Identification of a Recombinant Live Attenuated Respiratory Syncytial Virus Vaccine Candidate That Is Highly Attenuated in Infants.", Journal of Infectious Diseases, 191(7): 1093-1104.
Mallipeddi, et al., (1992), "Sequence comparison between the phosphoprotein mRNAs of human and bovine respiratory syncytial viruses identifies a divergent domain in the predicted protein.", The Journal of general virology, 73(Pt 9): 2441-2444.
Mallipeddi, et al., (1993), "Sequence variability of the glycoprotein gene of bovine respiratory syncytial virus.", Journal of General Virology, 74(9): 2001-2004.

(Continued)

*Primary Examiner* — Barry A Chestnut
(74) *Attorney, Agent, or Firm* — Emory Patent Group

(57) ABSTRACT

In certain embodiments, the disclosure relates to vectors containing bacterial nucleic acid sequences and a paramyxovirus gene. Typically, the expression vector comprises a bacterial artificial chromosome (BAC), and a nucleic acid sequence comprising a respiratory syncytial virus (RSV) gene in operable combination with a regulatory element and optionally a reporter gene.

9 Claims, 5 Drawing Sheets

Specification includes a Sequence Listing.

(56) References Cited

OTHER PUBLICATIONS

Maniatis, et al., (1987), "Regulation of inducible and tissue-specific gene expression.", Science, 236(4806): 1237-1245.
Merzlyak, et al., (2007), "Bright monomeric red fluorescent protein with an extended fluorescence lifetime.", Nat Meth, 4(7): 555-557.
Needleman, et al., (1970), "A general method applicable to the search for similarities in the amino acid sequence of two proteins.", Journal of Molecular Biology, 48(3): 443-453.
Pastey, et al., (1993), "Structure and sequence comparison of bovine respiratory syncytial virus fusion protein.", Virus Research, 29(2): 195-202.
Pastey, et al., (1995), "Nucleotide sequence analysis of the nonstructural NS1 (1C) and NS2 (1B) protein genes of bovine respiratory syncytial virus.", Journal of General Virology, 76(1): 193-197.
Pearson, et al., (1988), "Improved tools for biological sequence comparison.", Proceedings of the National Academy of Sciences, 85(8): 2444-2448.
Randhawa, et al., (1995), "Nucleotide Sequences of the Genes Encoding the Putative Attachment Glycoprotein (G) of Mouse and Tissue Culture-Passaged Strains of Pneumonia Virus of Mice.", Virology, 207(1): 240-245.
Roth, et al., (2011), "Recovery of infectious virus from full-length cowpox virus (CPXV) DNA cloned as a bacterial artificial chromosome (BAC).", Vet Res, 42(1): 3.
Shcherbo, et al., (2009), "Far-red fluorescent tags for protein imaging in living tissues." Biochem J 418(3): 567-574.
Shizuya, et al., (1992), "Cloning and stable maintenance of 300-kilobase-pair fragments of human DNA in *Escherichia coli* using an F-factor-based vector.", Proceedings of the National Academy of Sciences, 89(18): 8794-8797.
Shizuya, et al., (2001), "The development and applications of the bacterial artificial chromosome cloning system.", The Keio Journal of Medicine, 50(1): 26-30.
Skiadopoulos, et al., (2006), "Individual contributions of the human metapneumovirus F, G, and SH surface glycoproteins to the induction of neutralizing antibodies and protective immunity.", Virology, 345(2): 492-501.
Smith, et al., (1981), "Comparison of biosequences.", Advances in Applied Mathematics, 2(4): 482-489.
Voss, et al., (1986), "The role of enhancers in the regulation of cell-type-specific transcriptional control.", Trends in Biochemical Sciences, 11(7): 287-289.
Warming, et al., (2005), "Simple and highly efficient BAC recombineering using galK selection.", Nucleic Acids Research, 33(4): e36.
Zamora, et al., (1992), "Sequence analysis of M2 mRNA of bovine respiratory syncytial virus obtained from an F-M2 dicistronic mRNA suggests structural homology with that of human respiratory syncytial virus.", Journal of General Virology, 73(3): 737-741.
Zamora, et al., (1992), "Gene junction sequences of bovine respiratory syncytial virus.", Virus Research, 24(1): 115-121.

\* cited by examiner

FIG. 3E

SEQUENCE LISTING

<160> NUMBER OF SEQ ID NOS: 6

<210> SEQ ID NO 1
<211> LENGTH: 5459
<212> TYPE: DNA
<213> ORGANISM: Artificial
<220> FEATURE:
<223> OTHER INFORMATION: Synthetic construct

<400> SEQUENCE: 1

| | | | | | | |
|---|---|---|---|---|---|---|
| gggcagtgag | cggaaggccc | atgaggccag | ttaattaaga | ggtaccttcg | aaacgaaatt | 60 |
| aatacgactc | actataggga | gttttttcgc | gtctgatgag | gccgttaggc | cgaaactcct | 120 |
| ctccggagtc | acgcgaaaaa | atgcgtacaa | caaacttgca | taaaccaaaa | aaatggggca | 180 |
| aataagaatt | tgataagtac | cacttaaatt | taactcccct | gcttagcgat | ggtgagcgag | 240 |
| ctgattaagg | agaacatgca | catgaagctg | tacatggagg | gcaccgtgaa | caaccaccac | 300 |
| ttcaagtgca | catccgaggg | cgaaggcaag | ccctacgagg | gcacccagac | catgagaatc | 360 |
| aaggcggtcg | agggcggccc | tctccccttc | gccttcgaca | tcctggctac | cagcttcatg | 420 |
| tacggcagca | aaaccttcat | caaccacacc | cagggcatcc | ccgacttctt | taagcagtcc | 480 |
| ttccccgagg | gcttcacatg | ggagagagtc | accacatacg | aagacggggg | cgtgctgacc | 540 |
| gctacccagg | acaccagcct | ccaggacggc | tgcctcatct | acaacgtcaa | gatcagaggg | 600 |
| gtgaacttcc | catccaacgg | ccctgtgatg | cagaagaaaa | cactcggctg | ggaggcctcc | 660 |
| accgagaccc | tgtaccccgc | tgacggcggc | ctggaaggca | gagccgacat | ggccctgaag | 720 |
| ctcgtgggcg | ggggccacct | gatctgcaac | ttgaagacca | catacagatc | caagaaaccc | 780 |
| gctaagaacc | tcaagatgcc | cggcgtctac | tatgtggaca | gaagactgga | agaatcaag | 840 |
| gaggccgaca | agagaccta | cgtcgagcag | cacgaggtgg | ctgtggccag | atactgcgac | 900 |
| ctccctagca | aactgggca | cagatgagta | ttcaattata | gttattaaaa | acttaacaga | 960 |
| agacaaaaat | gggcaaata | agaatttgat | aagtaccact | taaatttaac | tcccttgctt | 1020 |
| agcgatgggc | agcaattcat | tgagtatgat | aaaagttaga | ttacaaaatt | tgtttgacaa | 1080 |
| tgatgaagta | gcattgttaa | aaataacatg | ctatactgat | aaattaatac | atttaactaa | 1140 |
| cgctttggct | aaggcagtga | tacatacaat | caaattgaat | ggcattgtgt | ttgtgcatgt | 1200 |
| tattacaagt | agtgatattt | gccctaataa | taatattgta | gtaaaatcca | atttcacaac | 1260 |
| aatgccagta | ctacaaaatg | gaggttatat | atgggaaatg | atggaattaa | cacattgctc | 1320 |
| tcaacctaat | ggtctactag | atgacaattg | tgaaattaaa | ttctccaaaa | aactaagtga | 1380 |
| ttcaacaatg | accaattata | tgaatcaatt | atctgaatta | cttggatttg | atcttaatcc | 1440 |
| ataaattata | attaatatca | actagcaaat | caatgtcact | aacaccatta | gttaatataa | 1500 |
| aacttaacag | aagacaaaaa | tggggcaaat | aaatcaattc | agccaaccca | accatggaca | 1560 |
| caacccacaa | tgataataca | ccacaaagac | tgatgatcac | agacatgaga | ccgttgtcac | 1620 |
| ttgagaccat | aataacatca | ctaaccagag | acatcataac | acacaaattt | atatacttga | 1680 |
| taaatcatga | atgcatagtg | agaaaacttg | atgaaagaca | ggccacattt | acattcctgg | 1740 |
| tcaactatga | atgaaactta | ttacacaaag | taggaagcac | taaatataaa | aaatatactg | 1800 |
| aatacaacac | aaaatatggc | actttcccta | tgccaatatt | catcaatcat | gatgggttct | 1860 |
| tagaatgcat | tggcattaag | cctacaaagc | atactcccat | aatatacaag | tatgatctca | 1920 |
| atccataaat | ttcaacacaa | tattcacaca | atctaaaaca | acaactctat | gcataactat | 1980 |
| actccatagt | ccagatggag | cctgaaaatt | atagtaattt | aaaattaagg | agagatataa | 2040 |

```
gatagaagat ggggcaaata caaagatggc tcttagcaaa gtcaagttga atgatacact    2100
caacaaagat caacttctgt catccagcaa atacaccatc aacggagca caggagatag    2160 tattgatact cctaattatg atgtgcagaa acacatcaat aagttatgtg gcatgttatt    2220
aatcacagaa gatgctaatc ataaattcac tgggttaata ggtatgttat atgcgatgtc    2280
taggttagga agagaagaca ccataaaaat actcagagat gcgggatatc atgtaaaagc    2340
aaatggagta gatgtaacaa cacatcgtca agacattaat ggaaaagaaa tgaaatttga    2400
agtgttaaca ttggcaagct taacaactga aattcaaatc aacattgaga tagaatctag    2460
aaaatcctac aaaaaaatgc taaagaaat gggagaggta gctccagaat acaggcatga    2520
ctctcctgat tgtgggatga taatattatg tatagcagca ttagtaataa ctaaattagc    2580
agcaggggac agatctggtc ttacagccgt gattaggaga gctaataatg tcctaaaaaa    2640
tgaaatgaaa cgttacaaag cttactacc caaggacata gccaacagct ctatgaagt    2700 gtttgaaaaa catccccact ttatagatgt ttttgttcat tttggtatag cacaatcttc    2760
taccagaggt ggcagtagag ttgaagggat ttttgcagga ttgtttatga atgcctatgg    2820
tgcagggcaa gtgatgttac ggtggggagt cttagcaaaa tcagttaaaa atattatgtt    2880
aggacatgct agtgtgcaag cagaaatgga acaagttgtt gaggtttatg aatatgccca    2940
aaaattgggt ggtgaagcag gattctacca tatattgaac aacccaaaag catcattatt    3000
atctttgact caatttcctc acttctccag tgtagtatta ggcaatgctg ctggcctagg    3060
cataatggga gagtacagag gtacaccgag gaatcaagat ctatatgatg cagcaaaggc    3120
atatgctgaa caactcaaag aaaatggtgt gattaactac agtgtactag acttgacagc    3180
agaagaacta gaggctatca acatcagct taatccaaaa gataatgatg tagagctttg    3240
agttaataaa aaatggggca aataaatcat catggaaaag tttgctcctg aattccatgg    3300
agaagatgca acaacagggg ctactaaatt cctagaatca ataaagggca aattcacatc    3360
acccaaagat cccaagaaaa aagatagtat catatctgtc aactcaatag atatagaagt    3420
aaccaaagaa agccctataa catcaaattc aactattatc aacccaacaa atgagacaga    3480
tgatactgca gggaacaagc ccaattatca agaaaaacct ctagtaagtt tcaaagaaga    3540
ccctacacca agtgataatc ccttttctaa actatacaaa gaaaccatag aaacatttga    3600
taacaatgaa gaagaatcca gctattcata cgaagaaata aatgatcaga caaacgataa    3660
tataacagca agattagata ggattgatga aaaattaagt gaaatactag gaatgcttca    3720
cacattagta gtggcaagtg caggacctac atctgctcgg gatggtataa gagatgccat    3780
gattggttta agagaagaaa tgatagaaaa atcagaact gaagcattaa tgaccaatga    3840
cagattagaa gctatggcaa gactcaggaa tgaggaaagt gaaaagatgg caaaagacac    3900
atcagatgaa gtgtctctca atccaacatc agagaaattg aacaacctat tggaagggaa    3960
tgatagtgac aatgatctat cacttgaaga tttctgatta gttaccactc ttcacatcaa    4020
cacacaatac caacagaaga ccaacaaact aaccaaccca atcatccaac caaacatcca    4080
tccgccaatc agccaaacag ccaacaaaac aaccagccaa tccaaaacta accaccgga    4140 aaaaatctat aatatagtta caaaaaaagg aaagggtggg gcaaatatgg aaacatacgt    4200
gaacaagctt cacgaaggct ccacatacac agctgctgtt caatacaatg tcttagaaaa    4260
agacgatgac cctgcatcac ttacaatatg ggtgcccatg ttccaatcat ctatgccagc    4320
agatttactt ataaaagaac tagctaatgt caacatacta gtgaaacaaa tatccacacc    4380
```

```
caagggacct tcactaagag tcatgataaa ctcaagaagt gcagtgctag cacaaatgcc   4440
cagcaaattt accatatgcg ctaatgtgtc cttggatgaa agaagcaaac tagcatatga   4500
tgtaaccaca ccctgtgaaa tcaaggcatg tagtctaaca tgcctaaaat caaaaaatat   4560
gttgactaca gttaaagatc tcactatgaa gacactcaac cctacacatg atattattgc   4620
tttatgtgaa tttgaaaaca tagtaacatc aaaaaaagtc ataataccaa catacctaag   4680
atccatcagt gtcagaaata aagatctgaa cacacttgaa aatataacaa ccactgaatt   4740
caaaaatgct atcacaaatg caaaaatcat cccttactca ggattactat tagtcatcac   4800
agtgactgac aacaaggag cattcaaata cataaagcca caaagtcaat tcatagtaga    4860
tcttggagct tacctagaaa agaaagtat atattatgtt accacaaatt ggaagcacac     4920
agctacacga tttgcaatca aacccatgga agattaacct ttttcctcta catcagtgtg   4980
ttaattcata caaactttct acctacattc ttcacttcac catcacaatc acaaacactc   5040
tgtggttcaa ccaatcaaac aaaacttatc tgaagtccca gatcatccca agtcattgtt   5100
tatcagatct agtactcaaa taagttaata aaaaatatac acatggacgt ccatggggca   5160
aataatcatt ggaggaaatc caactaatca caatatctgt taacatagac aagtccacac   5220
accatacaga atcaaccaat ggaaaataca tccataacaa tagaattctc aagcaaattc   5280
tggccttact ttacactaat acacatgatc acaacaataa tctctttgct aatcataatc   5340
tccatcatga ttgcaatact aaacaaactt tgtgaatata cgtattcca taacaaaacc     5400 tttgagttac caagagctca tggcgcgcct aggccttgac ggccttccgc caattcgcc    5459
```

<210> SEQ ID NO 2  
<211> LENGTH: 4523  
<212> TYPE: DNA  
<213> ORGANISM: Artificial  
<220> FEATURE:  
<223> OTHER INFORMATION: Synthetic construct

<400> SEQUENCE: 2

```
ttagggccca acaatgaact aggatatcaa gactaacaat aacattgggg caaatgcaaa    60
catgtccaaa acaaggacc aacgcaccgc taagacatta gaaaggacct gggacactct    120
caatcattta ttattcatat catcgtgctt atataagtta aatcttaaat ctgtagcaca    180
aatcacatta tccattctgg caatgataat ctcaacttca cttataattg cagccatcat   240
attcatagcc tcggcaaacc acaaagtcac accaacaact gcaatcatac aagatgcaac   300
aagccagatc aagaacacaa ccccaacata cctcacccag aatcctcagc ttggaatcag   360
tccctctaat ccgtctgaaa ttacatcaca aatcaccacc atactagctt caacaacacc   420
aggagtcaag tcaaccctgc aatccacaac agtcaagacc aaaaacacaa caacaactca   480
aacacaaccc agcaagccca ccacaaaaca acgccaaaac aaaccaccaa gcaaacccaa   540
taatgatttt cactttgaag tgttcaactt tgtaccctgc agcatatgca gcaacaatcc   600
aacctgctgg gctatctgca aaagaatacc aaacaaaaaa ccaggaaaga aaccactac    660 caagcccaca aaaaaaccaa ccctcaagac aaccaaaaaa gatcccaaac ctcaaaccac   720
taaatcaaag gaagtaccca ccaccaagcc cacagaagag ccaaccatca acaccaccaa   780
aacaaacatc ataactacac tactcaccct caacaccaca ggaaatccag aactcacaag   840
tcaaatggaa accttccact caacttcctc cgaaggcaat ccaagccctt ctcaagtctc   900
tacaacatcc gagtacccat cacaaccttc atctccaccc aacacaccac gccagtagtt    960
acttaaaaac atattatcac aaaaggcctt gaccaaccgc ggagaatcaa aataaactct   1020
```

```
gggggcaaata acaatggagt tgccaatcct caaagcaaat gcaattacca caatcctcgc   1080
tgcagtcaca ttttgctttg cttctagtca aacatcact gaagaatttt atcaatcaac    1140
atgcagtgca gttagcaaag gctatcttag tgctctaaga actggttggt atactagtgt   1200
tataactata gaattaagta atatcaagaa aaataagtgt aatggaacag atgctaaggt   1260
aaaattgatg aaacaagaat tagataaata taaaaatgct gtaacagaat tgcagttgct   1320
catgcaaagc acaccagcag caaacaatcg agccagaaga gaactaccaa ggtttatgaa   1380
ttatacactc aacaatacca aaaaaccaa tgtaacatta agcaagaaaa ggaaaagaag    1440
atttcttggt tttttgttag gtgttggatc tgcaatcgcc agtggcattg ctgtatctaa   1500
ggtcctgcac ttagaaggag aagtgaacaa gatcaaaagt gctctactat ccacaaacaa   1560
ggccgtagtc agcttatcaa atggagttag tgtcttaacc agcagagtgt tagacctcaa   1620
aaactatata gataaacaat tgttacctat tgtgaataag caaagctgca gaatatcaaa   1680
tatagaaact gtgatagagt tccaacaaaa gaacaacaga ctactagaga ttaccaggga   1740
atttagtgtt aatgcaggtg taactacacc tgtaagcact tacatgttaa ctaatagtga   1800
attattgtca ttaatcaatg atatgcctat aacaaatgat cagaaaaagt taatgtccaa   1860
caatgttcaa atagttagac agcaaagtta ctctatcatg tccataataa agaggaagt   1920 cttagcatat gtagtacaat taccactata tggtgtgata gatacacctt gttggaaatt   1980
acacacatcc cctctatgta caaccaacac aaaagaaggg tcaaacatct gtttaacaag   2040
aactgacaga ggatggtact gtgacaatgc aggatcagta tctttcttcc cacaagctga   2100
aaaatgtaaa gttcaatcga atcgagtatt ttgtgacaca atgtacagtt taacattacc   2160
aagtgaagta aatctctgca atgttgacat attcaatccc aaatatgatt gtaaaattat   2220
gacttcaaaa acagatgtaa gcagctccgt tatcacatct ctaggagcca ttgtgtcatg   2280
ctatggcaaa actaaatgta cagcatccaa taaaaatcgt ggaatcataa agacattttc   2340
taacgggtgt gattatgtat caaataaagg ggtggacact gtgtctgtag gtaacacatt   2400
atattatgta aataagcaag aaggcaaaag tctctatgta aaaggtgaac caataataaa   2460
tttctatgac ccattagtat tcccctctga tgaatttgat gcatcaatat ctcaagtcaa   2520
tgagaagatt aaccagagtt tagcatttat tcgtaaatcc gatgaattat tacataatgt   2580 aaaatgctggt aaatcaacca caatatcat gataactact ataattatag tgattatagt   2640
aatattgtta tcattaattg ctgttggact gctcctatac tgtaaggcca gaagcacacc   2700
aatcacacta agcaaggatc aactgagtgg tataaataat attgcattta gtaactgaat   2760
aaaaatagca cctaatcatg ttcttacaat ggtttactat ctgctcatag acaacccatc   2820
tatcattgga ttttcttaaa atctgaactt catcgaaact cttatctata accatctca   2880 cttacactat ttaagtagat tcctagttta tagttatata aaacacaatt gaatgccagt   2940
cgaccttacc atctgtaaaa atgaaaactg ggcaaatat gtcacgaagg aatccttgca   3000
aatttgaaat tcgaggtcat tgcttaaatg gtaagaggtg tcatttagt cataattatt   3060 ttgaatggcc accccatgca ctgcttgtaa gacaaaactt tatgttaaac agaatactta   3120
agtctatgga taaaagtata gatacctat cagaaataag tggagctgca gagttggaca   3180
gaacagaaga gtatgctctt ggtgtagttg gagtgctaga gagttatata ggatcaataa   3240
acaatataac taaacaatca gcatgtgttg ccatgagcaa actcctcact gaactcaata   3300
gtgatgatat caaaaagctg agggacaatg aagagctaaa ttcacccaag ataagagtgt   3360
```

```
acaatactgt catatcatat attgaaagca acaggaaaaa caataaacaa actatccatc    3420
tgttaaaaag attgccagca gacgtattga agaaaaccat caaaaacaca ttggatatcc    3480
ataagagcat aaccatcaac aacccaaaag aatcaactgt tagtgataca aatgaccatg    3540
ccaaaaataa tgatactacc tgacaaatat ccttgtagta aacttccat  actaataaca    3600 agtagatgta gagttactat gtataatcaa agaacacac  tatatttcaa tcaaaacaac    3660
ccaaataacc atatgtactc accgaatcaa acattcaatg aaatccattg gacctctcaa    3720
gaattgattg acacaattca aaattttcta caacatctag gtattattga ggatatatat    3780
acaatatata tattagtgtc ataacactca attctaacac tcaccacatc gttacattat    3840
taattcaaac aattcaagtt gtgggacaaa atggatccca ttattaatgg aaattctgct    3900
aatgtttatc taaccgatag ttatttaaaa ggtgttatct ctttctcaga gtgtaatgct    3960
ttaggaagtt acatattcaa tggtccttat ctcaaaaatg attataccaa cttaattagt    4020
agacaaaatc cattaataga acacatgaat ctaaagaaac taaatataac acagtcctta    4080
atatctaagt atcataaagg tgaaataaaa ttagaagaac ctacttattt tcagtcatta    4140
cttatgacat acaagagtat gacctcgtca gaacagattg ctaccactaa tttacttaaa    4200
aagataataa gaagagctat agaaataagt gatgtcaaag tctatgctat attgaataaa    4260
ctagggctta agaaaaagga caagattaaa tccaacaatg gacaagatga agacaactca    4320
gttattacga ccataatcaa agatgatata ctttcagctg taatcaaaac aacactcttg    4380
aagaaattga tgtgttcaat gcaacatcct ccatcatggt taatacattg gtttaactta    4440
tacacaaaat taaacaacat attaacacag tatcgatggt acctcttaat taactggcct    4500
catgggcctt ccgctcactg ccc                                            4523
```

<210> SEQ ID NO 3
<211> LENGTH: 6369
<212> TYPE: DNA
<213> ORGANISM: Artificial
<220> FEATURE:
<223> OTHER INFORMATION: Synthetic construct

<400> SEQUENCE: 3

```
ggcgaattgg cggaaggccg tcaaggccta ggcgcgccat gagctcatcg atcaaatgag     60
gtaaaaaacc atgggtttac attgatagat aatcaaactc ttagtggatt tcaatttatt    120
ttgaaccaat atggttgtat agtttatcat aaggaactca aaagaattac tgtgacaacc    180
tataatcaat tcttgacatg gaagatatt  agccttagta gattaaatgt ttgtttaatt    240
acatggatta gtaactgctt gaacacatta aataaaagct taggcttaag atgcggattc    300
aataatgtta tcttgacaca actattcctt tatggagatt gtatactaaa gctatttcac    360 aatgagggt  tctacataat aaaagaggta gagggattta ttatgtctct aattttaaat    420
ataacagaag aagatcaatt cagaaaacga tttataata  gtatgctcaa caacatcaca    480
gatgctgcta ataaagctca gaaaaatctg ctatcaagag tatgtcatac attattagat    540
aagacagtgt ccgataatat aataaatggc agatggataa ttctattaag taagttcctt    600
aaattaatta agcttgcagg tgacaataac cttaacaatc tgagtgaact atatttttg     660 ttcagaatat ttggacaccc aatggtagat gaaagacaag ccatggatgc tgttaaaatt    720
aattgcaatg agaccaaatt ttacttgtta agcagtctga gtatgttaag aggtgccttt    780
atatatagaa ttataaaagg gtttgtaaat aattacaaca atggcctac  tttaagaaat    840 gctattgttt taccttaag  atggttaact tactataaac taaacactta tccttctttg    900
```

```
ttggaactta cagaaagaga tttgattgtg ttatcaggac tacgtttcta tcgtgagttt      960
cggttgccta aaaaagtgga tcttgaaatg attataaatg ataaagctat atcacctcct     1020
aaaaatttga tatggactag tttccctaga aattacatgc catcacacat acaaaactat     1080
atagaacatg aaaaattaaa attttccgag agtgataaat caagaagagt attagagtat     1140
tatttaagag ataacaaatt caatgaatgt gatttataca actgtgtagt taatcaaagt     1200
tatctcaaca accctaatca tgtggtatca ttgacaggca aagaaagaga actcagtgta     1260
ggtagaatgt ttgcaatgca accgggaatg ttcagacagg ttcaaatatt ggcagagaaa     1320
atgatagctg aaaacatttt acaattcttt cctgaaagtc ttacaagata tggtgatcta     1380
gaactacaaa aaatattaga attgaaagca ggaataagta acaaatcaaa tcgctacaat     1440
gataattaca acaattacat tagtaagtgc tctatcatca cagatctcag caaattcaat     1500
caagcatttc gatatgaaac gtcatgtatt tgtagtgatg tgctggatga actgcatggt     1560
gtacaatctc tattttcctg gttacattta actattcctc atgtcacaat aatatgcaca     1620
tataggcatg cacccccta tataggagat catattgtag atcttaacaa tgtagatgaa     1680
caaagtggat tatatagata tcacatgggt ggcatcgaag ggtggtgtca aaaactgtgg     1740
accatagaag ctatatcact attggatcta atatctctca aagggaaatt ctcaattact     1800
gctttaatta tggtgacaa tcaatcaata gatataagca aaccaatcag actcatggaa     1860
ggtcaaactc atgctcaagc agattatttg ctagcattaa atagccttaa attactgtat     1920
aaagagtatg caggcatagg ccacaaatta aaaggaactg agacttatat atcacgagat     1980
atgcaattta tgagtaaaac aattcaacat aacggtgtat attcccagc tagtataaag     2040 aaagtcctaa gagtgggacc gtggataaac actatacttg atgatttcaa agtgagtcta     2100
gaatctatag gtagtttgac acaagaatta gaatatagag gtgaaagtct attatgcagt     2160
ttaatattta gaaatgtatg gttatataat cagattgctc tacaattaaa aaatcatgca     2220
ttatgtaaca ataaactata tttggacata ttaaaggttc tgaaacactt aaaaaccttt     2280
tttaatcttg ataatattga tacagcatta acattgtata tgaatttacc catgttattt     2340
ggtggtggtg atcccaactt gttatatcga agtttctata agaactcc tgacttcctc     2400 acagaggcta tagttcactc tgtgttcata cttagttatt atacaaacca tgacttaaaa     2460
gataaacttc aagatctgtc agatgataga ttgaataagt tcttaacatg cataatcacg     2520
tttgacaaaa accctaatgc tgaattcgta acattgatga gagatcctca agctttaggg     2580
tctgagagac aagctaaaat tactagcgaa atcaatagac tggcagttac agaggttttg     2640
agtacagctc caaacaaaat attctccaaa agtgcacaac attatactac tacagagata     2700
gatctaaatg atattatgca aaatatagaa cctacatatc ctcatgggct aagagttgtt     2760
tatgaaagtt tacccttta taaagcagag aaaatagtaa atcttatatc aggtacaaaa     2820
tctataacta acatactgga aaaaacttct gccatagact aacagatat tgatagagcc     2880 actgagatga tgaggaaaaa cataactttg cttataagga tacttccatt ggattgtaac     2940
agagataaaa gagagatatt gagtatggaa aacctaagta ttactgaatt aagcaaatat     3000
gttagggaaa gatcttggtc tttatccaat atagttggtg ttacatcacc cagtatcatg     3060
tatacaatgg acatcaaata tactacaagc actatatcta gtggcataat tatagagaaa     3120
tataatgtta acagtttaac acgtggtgag agaggaccca ctaaacctatg ggttggttca     3180 tctacacaag agaaaaaaac aatgccagtt tataatagac aagtcttaac caaaaaacag     3240
```

```
agagatcaaa tagatctatt agcaaaattg gattgggtgt atgcatctat agataacaag   3300
gatgaattca tggaagaact cagcatagga acccttgggt taacatatga aaaggccaag   3360
aaattatttc cacaatattt aagtgtcaat tatttgcatc gccttacagt cagtagtaga   3420
ccatgtgaat tccctgcatc aataccagct tatagaacaa caaattatca ctttgacact   3480
agccctatta atcgcatatt aacagaaaag tatggtgatg aagatattga catagtattc   3540
caaaactgta taagctttgg ccttagttta atgtcagtag tagaacaatt tactaatgta   3600
tgtcctaaca gaattattct catacctaag cttaatgaga tacatttgat gaaacctccc   3660
atattcacag gtgatgttga tattcacaag ttaaaacaag tgatacaaaa acagcatatg   3720
tttttaccag acaaaataag tttgactcaa tatgtggaat tattcttaag taataaaaca   3780
ctcaaatctg gatctcatgt taattctaat ttaatattgg cacataaaat atctgactat   3840
tttcataata cttacatttt aagtactaat ttagctggac attggattct gattatacaa   3900
cttatgaaag attctaaagg tatttttgaa aaagattggg gagagggata taactgat    3960
catatgttta ttaatttgaa agttttcttc aatgcttata agacctatct cttgtgtttt   4020
cataaaggtt atggcaaagc aaagctggag tgtgatatga acacttcaga tcttctatgt   4080
gtattggaat taatagacag tagttattgg aagtctatgt ctaaggtatt tttagaacaa   4140
aaagttatca aatacattct tagccaagat gcaagtttac atagagtaaa aggatgtcat   4200
agcttcaaat tatggtttct taaacgtctt aatgtagcag aattcacagt ttgcccttgg   4260
gttgttaaca tagattatca tccaacacat atgaaagcaa tattaactta tatagatctt   4320
gttagaatgg gattgataaa tatagataga atacacatta aaaataaaca caaattcaat   4380
gatgaatttt atacttctaa tctcttctac attaattata acttctcaga taatactcat   4440
ctattaacta aacatataag gattgctaat tctgaattag aaaataatta caacaaatta   4500
tatcatccta caccagaaac cctagagaat atactagcca atccgattaa agtaatgac    4560
aaaaagacac tgaatgacta ttgtataggt aaaaatgttg actcaataat gttaccattg   4620
ttatctaata agaagcttat taaatcgtct gcaatgatta gaaccaatta cagcaaacaa   4680
gatttgtata atttattccc tatggttgtg attgatagaa ttatagatca ttcaggcaat   4740
acagccaaat ccaaccaact ttacactact acttcccacc aaatatcttt agtgcacaat   4800
agcacatcac tttactgcat gcttccttgg catcatatta atagattcaa ttttgtattt   4860
agttctacag gttgtaaaat tagtatagag tatatttaa aagatcttaa aattaaagat   4920
cccaattgta tagcattcat aggtgaagga gcagggaatt tattattgcg tacagtagtg   4980
gaacttcatc ctgacataag atatatttac agaagtctga aagattgcaa tgatcatagt   5040
ttacctattg agttttttaag gctgtacaat ggacatatca acattgatta tggtgaaaat   5100
ttgaccattc ctgctacaga tgcaaccaac acattcatt ggtcttattt acatataaag   5160
tttgctgaac ctatcagtct ttttgtctgt gatgccgaat tgtctgtaac agtcaactgg   5220
agtaaaatta atagaatg gagcaagcat gtaagaaagt gcaagtactg ttcctcagtt   5280
aataaatgta tgttaatagt aaatatcat gctcaagatg atattgattt caaattagac   5340
aatataacta tattaaaaac ttatgtatgc ttaggcagta agttaaaggg atcggaggtt   5400
tacttagtcc ttacaatagg tcctgcgaat atattcccag tatttaatgt agtacaaaat   5460
gctaaattga tactatcaag aaccaaaaat ttcatcatgc ctaagaaagc tgataaagag   5520
tctattgatg caaatattaa aagtttgata cccttctttt gttacccttat aacaaaaaaa   5580
ggaattaata ctgcattgtc aaaactaaag agtgttgtta gtggagatat actatcatat   5640
```

```
tctatagctg acgtaatga agttttcagc aataaactta taaatcataa gcatatgaac    5700
atcttaaaat ggttcaatca tgtttaaat ttcagatcaa cagaactaaa ctataaccat    5760
```
(Note: line 5760 as printed reads "atcttaaaat ggttcaatca tgtttaaat ttcagatcaa cagaactaaa ctataaccat")

```
ttatatatgg tagaatctac atatccttac ctaagtgaat tgttaaacag cttgacaacc    5820
aatgaactta aaaaactgat taaaatcaca ggtagtctgt tatacaactt tcataatgaa    5880
taatgaataa agatcttata ataaaaattc ccatagctat acactaacac tgtattcaat    5940
tatagttatt aaaaattaaa aatcgtacga tttttaaat aactttagt gaactaatcc    6000 taaagttatc attttaatct tggaggaata aatttaaacc ctaatctaat tggtttatat    6060
gtgtattaac taaattacga gatattagtt tttgacactt tttttctcgt gggtcggcat    6120
ggcatctcca cctcctcgcg gtccgacctg gcatccgaa ggaggacgca cgtccactcg    6180
gatggctaag ggagctgcta acaaagcccg aaaggaagct gagttggctg ctgccaccgc    6240
tgagcaataa ctagcataac cccttggggc ctctaaacgg gtcttgaggg gttttttgct    6300
gaaaggagga actatatacg cgtggtacct cttaattaac tggcctcatg ggccttccgc    6360
tcactgccc                                                           6369
```

<210> SEQ ID NO 4
<211> LENGTH: 39
<212> TYPE: DNA
<213> ORGANISM: Artificial
<220> FEATURE:
<223> OTHER INFORMATION: Synthetic construct

<400> SEQUENCE: 4

```
cgaattggga gctcttttat cgatgttgcc taggttta                            39
```

<210> SEQ ID NO 5
<211> LENGTH: 41
<212> TYPE: DNA
<213> ORGANISM: Artificial
<220> FEATURE:
<223> OTHER INFORMATION: Synthetic construct

<400> SEQUENCE: 5

```
cgcgtaaaac ctaggcaaca tcgataaaag agctcccaat t                        41
```

<210> SEQ ID NO 6
<211> LENGTH: 22620
<212> TYPE: DNA
<213> ORGANISM: Artificial
<220> FEATURE:
<223> OTHER INFORMATION: Synthetic construct

<400> SEQUENCE: 6

```
aaacggatcc ttcgaaacga aattaatacg actcactata gggaagtttt tcgcgtctga    60
tgaggccgtt aggccgaaac tcctctccgg agtcacgcga aaaatgcgt acaacaaact    120 tgcataaacc aaaaaaatgg ggcaaataag aatttgataa gtaccactta aatttaactc    180
ccttgcttag cgatggtgag cgagctgatt aaggagaaca tgcacatgaa gctgtacatg    240
gagggcaccg tgaacaacca ccacttcaag tgcacatccg agggcgaagg caagcccctac    300 gagggcaccc agaccatgag aatcaaggcg gtcgagggcg ccctctccc cttcgccttc    360 gacatcctgg ctaccagctt catgtacggc agcaaaacct tcatcaacca cacccagggc    420
atccccgact tctttaagca gtccttcccc gagggcttca catgggagag agtcaccaca    480
tacgaagacg ggggcgtgct gaccgctacc caggacacca gcctccagga cggctgcctc    540
```

```
atctacaacg tcaagatcag aggggtgaac ttcccatcca acggccctgt gatgcagaag      600
aaaacactcg gctgggaggc ctccaccgag accctgtacc ccgctgacgg cggcctggaa      660
ggcagagccg acatggccct gaagctcgtg ggcgggggcc acctgatctg caacttgaag      720
accacataca gatccaagaa acccgctaag aacctcaaga tgcccggcgt ctactatgtg      780
gacagaagac tggaaagaat caaggaggcc gacaaagaga cctacgtcga gcagcacgag      840
gtggctgtgg ccagatactg cgacctccct agcaaactgg ggcacagatg agtattcaat      900
tatagttatt aaaaacttaa cagaagacaa aaatggggca ataagaatt  tgataagtac      960 cacttaaatt taactcccctt gcttagcgat gggcagcaat tcattgagta tgataaaagt     1020
tagattacaa aatttgtttg acaatgatga agtagcattg ttaaaaataa catgctatac     1080
tgataaatta atacatttaa ctaacgctttt ggctaaggca gtgatacata caatcaaatt     1140
gaatggcatt gtgtttgtgc atgttattac aagtagtgat atttgcccta ataataatat     1200
tgtagtaaaa tccaatttca caacaatgcc agtactacaa aatggaggtt atatatggga     1260
aatgatggaa ttaacacatt gctctcaacc taatggtcta ctagatgaca attgtgaaat     1320
taaattctcc aaaaaactaa gtgattcaac aatgaccaat tatatgaatc aattatctga     1380
attacttgga tttgatctta atccataaat tataattaat atcaactagc aaatcaatgt     1440
cactaacacc attagttaat ataaaactta acagaagaca aaaatggggc aaataaatca     1500
attcagccaa cccaaccatg gacacaaccc acaatgataa tacaccacaa agactgatga     1560
tcacagacat gagaccgttg tcacttgaga ccataataac atcactaacc agagacatca     1620
taacacacaa atttatatac ttgataaatc atgaatgcat agtgagaaaa cttgatgaaa     1680
gacaggccac atttacattc ctggtcaact atgaaatgaa actattacac aaagtaggaa     1740
gcactaaata taaaaaatat actgaataca acacaaaata tggcactttc cctatgccaa     1800
tattcatcaa tcatgatggg ttcttagaat gcattggcat taagcctaca aagcatactc     1860
ccataatata caagtatgat ctcaatccat aaatttcaac acaatattca cacaatctaa     1920
aacaacaact ctatgcataa ctatactcca tagtccagat ggagcctgaa aattatagta     1980
atttaaaatt aaggagagat ataagataga agatggggca aatacaaaga tggctcttag     2040
caaagtcaag ttgaatgata cactcaacaa agatcaactt ctgtcatcca gcaaatacac     2100
catccaacgg agcacaggag atagtattga tactcctaat tatgatgtgc agaaacacat     2160
caataagtta tgtggcatgt tattaatcac agaagatgct aatcataaat tcactgggtt     2220
aataggtatg ttatatgcga tgtctaggtt aggaagagaa gacaccataa aaatactcag     2280
agatgcggga tatcatgtaa aagcaaatgg agtagatgta acaacacatc gtcaagacat     2340
taatggaaaa gaaatgaaat ttgaagtgtt aacattggca agcttaacaa ctgaaattca     2400
aatcaacatt gagatagaat ctagaaaatc ctacaaaaaa atgctaaaag aaatgggaga     2460
ggtagctcca gaatacaggc atgactctcc tgattgtggg atgataatat tatgtatagc     2520
agcattagta ataactaaat tagcagcagg ggacagatct ggtcttacag ccgtgattag     2580
gagagctaat aatgtcctaa aaaatgaaat gaaacgttac aaaggcttac tacccaagga     2640
catagccaac agcttctatg aagtgtttga aaaacatccc cactttatag atgtttttgt     2700
tcattttggt atagcacaat cttctaccag aggtggcagt agagttgaag gatttttgc      2760 aggattgttt atgaatgcct atggtgcagg gcaagtgatg ttacggtggg gagtcttagc     2820
aaaatcagtt aaaaatatta tgttaggaca tgctagtgtg caagcagaaa tggaacaagt     2880
tgttgaggtt tatgaatatg cccaaaaatt gggtggtgaa gcaggattct accatatatt     2940
```

-continued

```
gaacaaccca aaagcatcat tattatcttt gactcaattt cctcacttct ccagtgtagt    3000
attaggcaat gctgctggcc taggcataat gggagagtac agaggtacac cgaggaatca    3060
agatctatat gatgcagcaa aggcatatgc tgaacaactc aaagaaaatg gtgtgattaa    3120
ctacagtgta ctagacttga cagcagaaga actagaggct atcaaacatc agcttaatcc    3180
aaaagataat gatgtagagc tttgagttaa taaaaaatgg ggcaaataaa tcatcatgga    3240
aaagtttgct cctgaattcc atggagaaga tgcaaacaac agggctacta aattcctaga    3300
atcaataaag ggcaaattca catcacccaa agatcccaag aaaaagata gtatcatatc     3360 tgtcaactca atagatatag aagtaaccaa agaaagccct ataacatcaa attcaactat    3420
tatcaaccca acaaatgaga cagatgatac tgcagggaac aagcccaatt atcaaagaaa    3480
acctctagta agtttcaaag aagacccta ccaagtgat aatccctttt ctaaactata      3540
caaagaaacc atagaaacat ttgataacaa tgaagaagaa tccagctatt catacgaaga    3600
aataaatgat cagacaaacg ataatataac agcaagatta gataggattg atgaaaaatt    3660
aagtgaaata ctaggaatgc ttcacacatt agtagtggca agtgcaggac ctacatctgc    3720
tcgggatggt ataagagatg ccatgattgg tttaagagaa gaaatgatag aaaaaatcag    3780
aactgaagca ttaatgacca atgacagatt agaagctatg caagactca ggaatgagga     3840 aagtgaaaag atggcaaaag acacatcaga tgaagtgtct ctcaatccaa catcagagaa    3900
attgaacaac ctattggaag ggaatgatag tgacaatgat ctatcacttg aagatttctg    3960
attagttacc actcttcaca tcaacacaca ataccaacag aagaccaaca aactaaccaa    4020
cccaatcatc aaccaaaca tccatccgcc aatcagccaa acagccaaca aacaaccag      4080 ccaatccaaa actaaccacc cggaaaaaat ctataatata gttacaaaaa aaggaaaggg    4140
tggggcaaat atggaaacat acgtgaacaa gcttcacgaa ggctccacat acacagctgc    4200
tgttcaatac aatgtcttag aaaaagacga tgaccctgca tcacttacaa tatgggtgcc    4260
catgttccaa tcatctatgc cagcagattt acttataaaa gaactagcta atgtcaacat    4320
actagtgaaa caaatatcca cacccaaggg accttcacta agagtcatga taaactcaag    4380
aagtgcagtg ctagcacaaa tgcccagcaa atttaccata tgcgctaatg tgtccttgga    4440
tgaaagaagc aaactagcat atgatgtaac cacaccctgt gaaatcaagg catgtagtct    4500
aacatgccta aaatcaaaaa atatgttgac tacagttaaa gatctcacta tgaagacact    4560
caaccctaca catgatatta ttgctttatg tgaatttgaa aacatagtaa catcaaaaaa    4620
agtcataata ccaacatacc taagatccat cagtgtcaga aataaagatc tgaacacact    4680
tgaaaatata acaaccactg aattcaaaaa tgctatcaca aatgcaaaaa tcatcccctta   4740 ctcaggatta ctattagtca tcacagtgac tgacaacaaa ggagcattca atacataaa     4800 gccacaaagt caattcatag tagatcttgg agcttaccta gaaaaagaaa gtatatatta    4860
tgttaccaca aattggaagc acacagctac acgatttgca atcaaaccca tggaagatta    4920 accttttttcc tctacatcag tgtgttaatt catacaaact ttctacctac attcttcact    4980
tcaccatcac aatcacaaac actctgtggt tcaaccaatc aaacaaaact tatctgaagt    5040
cccagatcat cccaagtcat tgtttatcag atctagtact caaataagtt aataaaaaat    5100
atacacatgg acgtccatgg ggcaaataat cattggagga aatccaacta atcacaatat    5160
ctgttaacat agacaagtcc acacaccata cagaatcaac caatggaaaa tacatccata    5220
acaatagaat tctcaagcaa attctggcct tactttacac taatacacat gatcacaaca    5280
```

```
ataatctctt tgctaatcat aatctccatc atgattgcaa tactaaacaa actttgtgaa    5340
tataacgtat tccataacaa aacctttgag ttaccaagag ctcgagttaa tacttgataa    5400
agtagttaat taaaaattag ggcccaacaa tgaactagga tatcaagact aacaataaca    5460
ttggggcaaa tgcaaacatg tccaaaaaca aggaccaacg caccgctaag acattagaaa    5520
ggacctggga cactctcaat catttattat tcatatcatc gtgcttatat aagttaaatc    5580
ttaaatctgt agcacaaatc acattatcca ttctggcaat gataatctca acttcactta    5640
taattgcagc catcatattc atagcctcgg caaaccacaa agtcacacca acaactgcaa    5700
tcatacaaga tgcaacaagc cagatcaaga acacaacccc aacatacctc acccagaatc    5760
ctcagcttgg aatcagtccc tctaatccgt ctgaaattac atcacaaatc accaccatac    5820
tagcttcaac aacaccagga gtcaagtcaa ccctgcaatc cacaacagtc aagaccaaaa    5880
acacaacaac aactcaaaca caacccagca agcccaccac aaaacaacgc caaaacaaac    5940
caccaagcaa acccaataat gattttcact ttgaagtgtt caactttgta ccctgcagca    6000
tatgcagcaa caatccaacc tgctgggcta tctgcaaaag aataccaaac aaaaaaccag    6060
gaaagaaaac cactaccaag cccacaaaaa accaaccct caagacaacc aaaaaagatc    6120
ccaaacctca aaccactaaa tcaaaggaag tacccaccac caagcccaca gaagagccaa    6180
ccatcaacac caccaaaaca aacatcataa ctacactact cacctccaac accacaggaa    6240
atccagaact cacaagtcaa atggaaacct tccactcaac ttcctccgaa ggcaatccaa    6300
gcccttctca gtctctaca acatccgagt acccatcaca accttcatct ccacccaaca    6360
caccacgcca gtagttactt aaaaacatat tatcacaaaa ggccttgacc aaccgcggag    6420
aatcaaaata aactctgggg caaataacaa tggagttgcc aatcctcaaa gcaaatgcaa    6480
ttaccacaat cctcgctgca gtcacatttt gctttgcttc tagtcaaaac atcactgaag    6540
aattttatca atcaacatgc agtgcagtta gcaaaggcta tcttagtgct ctaagaactg    6600
gttggtatac tagtgttata actatagaat taagtaatat caagaaaaat aagtgtaatg    6660
gaacagatgc taaggtaaaa ttgatgaaac aagaattaga taaatataaa aatgctgtaa    6720
cagaattgca gttgctcatg caaagcacac cagcagcaaa caatcgagcc agaagagaac    6780
taccaaggtt tatgaattat acactcaaca ataccaaaaa aaccaatgta acattaagca    6840
agaaaaggaa aagaagattt cttggttttt tgttaggtgt tggatctgca atcgccagtg    6900
gcattgctgt atctaaggtc ctgcacttag aaggagaagt gaacaagatc aaaagtgctc    6960
tactatccac aaaacaaggc cgtagtcagc tatcaaatgg agttagtgtc ttaaccagca    7020
gagtgttaga cctcaaaaac tatatagata aacaattgtt acctattgtg aataagcaaa    7080
gctgcagaat atcaaatata gaactgtga tagttccca acaaaagaac aacagactac    7140
tagagattac cagggaattt agtgttaatg caggtgtaac tacacctgta agcacttaca    7200
tgttaactaa tagtgaatta ttgtcattaa tcaatgatat gcctataaca aatgatcaga    7260
aaaagttaat gtccaacaat gttcaaatag ttagacagca aagttactct atcatgtcca    7320
taataaaaga ggaagtctta gcatatgtag tacaattacc actatatggt gtgatagata    7380
caccttgttg gaaattacac acatcccctc tatgtacaac caacacaaaa gaagggtcaa    7440
acatctgttt aacaagaact gacagaggat ggtactgtga caatgcagga tcagtatctt    7500
tcttcccaca agctgaaaaa tgtaaagttc aatcgaatcg agtattttgt gacacaatgt    7560
acagtttaac attaccaagt gaagtaaatc tctgcaatgt tgacatattc aatcccaaat    7620
atgattgtaa aattatgact tcaaaaacag atgtaagcag ctccgttatc acatctctag    7680
```

```
gagccattgt gtcatgctat ggcaaaacta aatgtacagc atccaataaa aatcgtggaa    7740
tcataaagac attttctaac gggtgtgatt atgtatcaaa taaaggggtg gacactgtgt    7800
ctgtaggtaa cacattatat tatgtaaata agcaagaagg caaaagtctc tatgtaaaag    7860
gtgaaccaat aataaatttc tatgacccat tagtattccc ctctgatgaa tttgatgcat    7920
caatatctca agtcaatgag aagattaacc agagtttagc atttattcgt aaatccgatg    7980
aattattaca taatgtaaat gctggtaaat caaccacaaa tatcatgata actactataa    8040
ttatagtgat tatagtaata ttgttatcat taattgctgt tggactgctc ctatactgta    8100
aggccagaag cacaccaatc acactaagca aggatcaact gagtggtata aataatattg    8160
catttagtaa ctgaataaaa atagcaccta atcatgttct tacaatggtt tactatctgc    8220
tcatagacaa cccatctatc attggatttt cttaaaatct gaacttcatc gaactctta    8280 tctataaacc atctcactta cactatttaa gtagattcct agtttatagt tatataaaac    8340
acaattgaat gccagtcgac cttaccatct gtaaaaatga aaactggggc aaatatgtca    8400
cgaaggaatc cttgcaaatt tgaaattcga ggtcattgct taaatggtaa gaggtgtcat    8460
tttagtcata attattttga atggccaccc catgcactgc ttgtaagaca aaactttatg    8520
ttaaacagaa tacttaagtc tatggataaa agtatagata ccttatcaga ataagtgga    8580 gctgcagagt tggacagaac agaagagtat gctcttggtg tagttggagt gctagagagt    8640
tatataggat caataaacaa tataactaaa caatcagcat gtgttgccat gagcaaactc    8700
ctcactgaac tcaatagtga tgatatcaaa aagctgaggg acaatgaaga gctaaattca    8760
cccaagataa gagtgtacaa tactgtcata tcatatattg aaagcaacag gaaaaacaat    8820
aaacaaacta tccatctgtt aaaaagattg ccagcagacg tattgaagaa accatcaaa    8880 aacacattgg atatccataa gagcataacc atcaacaacc caaaagaatc aactgttagt    8940
gatacaaatg accatgccaa aaataatgat actacctgac aaatatcctt gtagtataac    9000
ttccatacta ataacaagta gatgtagagt tactatgtat aatcaaaaga acacactata    9060
tttcaatcaa acaacccaa ataaccatat gtactcaccg aatcaaacat tcaatgaaat    9120
ccattggacc tctcaagaat tgattgacac aattcaaaat tttctacaac atctaggtat    9180
tattgaggat atatacaa tatatatatt agtgtcataa cactcaattc taacactcac    9240
cacatcgtta cattattaat tcaaacaatt caagttgtgg gacaaaatgg atcccattat    9300
taatggaaat tctgctaatg tttatctaac cgatagttat ttaaaaggtg ttatctcttt    9360
ctcagagtgt aatgctttag gaagttacat attcaatggt ccttatctca aaaatgatta    9420
taccaactta attagtagac aaaatccatt aatagaacac atgaatctaa agaaactaaa    9480
tataacacag tccttaatat ctaagtatca taaaggtgaa ataaaattag aagaacctac    9540 ttatttcag tcattactta tgacatacaa gagtatgacc tcgtcagaac agattgctac    9600
cactaattta cttaaaaaga taataagaag agctatagaa ataagtgatg tcaaagtcta    9660
tgctatattg aataaactag ggcttaaaga aaaggacaag attaaatcca acaatggaca    9720
agatgaagac aactcagtta ttacgaccat aatcaaagat gatatacttt cagctgttaa    9780
agataatcaa tctcatctta agcagacaa aaatcactct acaaaacaaa aagacacaat    9840
caaaacaaca ctcttgaaga aattgatgtg ttcaatgcaa catcctccat catggttaat    9900
acattggttt aacttataca caaaattaaa caacatatta acacagtatc gatcaaatga    9960
ggtaaaaaac catgggttta cattgataga taatcaaact cttagtggat ttcaattat   10020
```

```
tttgaaccaa tatggttgta tagtttatca taaggaactc aaaagaatta ctgtgacaac    10080
ctataatcaa ttcttgacat ggaaagatat tagccttagt agattaaatg tttgtttaat    10140
tacatggatt agtaactgct tgaacacatt aaataaaagc ttaggcttaa gatgcggatt    10200
caataatgtt atcttgacac aactattcct ttatggagat tgtatactaa agctatttca    10260
caatgagggg ttctacataa taaaagaggt agagggattt attatgtctc taattttaaa    10320
tataacagaa gaagatcaat tcagaaaacg atttttataa agtatgctca acaacatcac    10380
agatgctgct aataaagctc agaaaaatct gctatcaaga gtatgtcata cattattaga    10440
taagacagtg tccgataata taataaatgg cagatggata attctattaa gtaagttcct    10500
taaattaatt aagcttgcag gtgacaataa ccttaacaat ctgagtgaac tatatttttt    10560
gttcagaata tttggacacc caatggtaga tgaaagacaa gccatggatg ctgttaaaat    10620
taattgcaat gagaccaaat tttacttgtt aagcagtctg agtatgttaa gaggtgcctt    10680
tatatataga attataaaag ggtttgtaaa taattacaac agatggccta ctttaagaaa    10740
tgctattgtt ttacccttaa gatggttaac ttactataaa ctaaacactt atccttcttt    10800
gttggaactt acagaaagag atttgattgt gttatcagga ctacgtttct atcgtgagtt    10860
tcggttgcct aaaaaagtgg atcttgaaat gattataaat gataaagcta tcacctcc     10920 taaaaatttg atatggacta gtttccctag aaattacatg ccatcacaca tacaaaacta    10980
tatagaacat gaaaaattaa aattttccga gagtgataaa tcaagaagag tattagagta    11040
ttatttaaga gataacaaat tcaatgaatg tgatttatac aactgtgtag ttaatcaaag    11100
ttatctcaac aaccctaatc atgtggtatc attgacaggc aaagaaagag aactcagtgt    11160
aggtagaatg tttgcaatgc aaccgggaat gttcagacag gttcaaatat ggcagagaa    11220 aatgatagct gaaaacattt tacaattctt tcctgaaagt cttacaagat atggtgatct    11280
agaactacaa aaaatattag aattgaaagc aggaataagt aacaaatcaa atcgctacaa    11340
tgataattac aacaattaca ttagtaagtg ctctatcatc acagatctca gcaaattcaa    11400
tcaagcattt cgatatgaaa cgtcatgtat ttgtagtgat gtgctggatg aactgcatgg    11460
tgtacaatct ctattttcct ggttacattt aactattcct catgtcacaa taatatgcac    11520 ataggcat gcacccccct ataggaga tcatattgta gatcttaaca atgtagatga    11580
acaaagtgga ttatatagat atcacatggg tggcatcgaa gggtggtgtc aaaaactgtg    11640
gaccatagaa gctatatcac tattggatct aatatctctc aaagggaaat tctcaattac    11700
tgctttaatt aatggtgaca atcaatcaat agatataagc aaaccaatca gactcatgga    11760
aggtcaaact catgctcaag cagattattt gctagcatta aatagcctta aattactgta    11820
taaagagtat gcaggcatag gccacaaatt aaaaggaact gagacttata tatcacgaga    11880
tatgcaattt atgagtaaaa caattcaaca taacggtgta tattacccag ctagtataaa    11940
gaaagtccta agagtgggac cgtggataaa cactatactt gatgatttca aagtgagtct    12000
agaatctata ggtagtttga cacaagaatt agaaatataga ggtgaaagtc tattatgcag    12060
tttaatattt agaaatgtat ggttatataa tcagattgct ctacaattaa aaaatcatgc    12120
attatgtaac aataaactat atttggacat attaaaggtt ctgaaacact taaaaacctt    12180
ttttaatctt gataatattg atacagcatt aacattgtat atgaatttac ccatgttatt    12240
tggtggtggt gatcccaact tgttatatcg aagtttctat agaagaactc ctgacttcct    12300
cacagaggct atagttcact ctgtgttcat acttagttat tatacaaacc atgacttaaa    12360
agataaactt caagatctgt cagatgatag attgaataag ttcttaacat gcataatcac    12420
```

```
gtttgacaaa aaccctaatg ctgaattcgt aacattgatg agagatcctc aagctttagg   12480
gtctgagaga caagctaaaa ttactagcga aatcaataga ctggcagtta cagaggtttt   12540
gagtacagct ccaaacaaaa tattctccaa aagtgcacaa cattatacta ctacagagat   12600
agatctaaat gatattatgc aaaatataga acctacatat cctcatgggc taagagttgt   12660
ttatgaaagt ttaccctttt ataaagcaga gaaaatagta aatcttatat caggtacaaa   12720
atctataact aacatactgg aaaaaacttc tgccatagac ttaacagata ttgatagagc   12780
cactgagatg atgaggaaaa acataacttt gcttataagg atacttccat tggattgtaa   12840
cagagataaa agagagatat tgagtatgga aaacctaagt attactgaat taagcaaata   12900
tgttagggaa agatcttggt ctttatccaa tatagttggt gttacatcac ccagtatcat   12960
gtatacaatg gacatcaaat atactacaag cactatatct agtggcataa ttatagagaa   13020
atataatgtt aacagtttaa cacgtggtga gagaggaccc actaaaccat gggttggttc   13080
atctacacaa gagaaaaaaa caatgccagt ttataataga caagtcttaa ccaaaaaaca   13140
gagagatcaa atagatctat tagcaaaatt ggattgggtg tatgcatcta tagataacaa   13200
ggatgaattc atggaagaac tcagcatagg aaccccttggg ttaacatatg aaaaggccaa   13260
gaaattattt ccacaatatt taagtgtcaa ttatttgcat cgccttacag tcagtagtag   13320
accatgtgaa ttccctgcat caataccagc ttatagaaca acaaattatc actttgacac   13380
tagccctatt aatcgcatat aacagaaaaa gtatggtgat gaagatattg acatagtatt   13440
ccaaaactgt ataagctttg gccttagttt aatgtcagta gtagaacaat ttactaatgt   13500
atgtcctaac agaattattc tcatacctaa gcttaatgag atacatttga tgaaacctcc   13560
catattcaca ggtgatgttg atattcacaa gttaaaacaa gtgatacaaa acagcatat    13620 gttttttacca gacaaaataa gtttgactca atatgtggaa ttattcttaa gtaataaaac   13680
actcaaatct ggatctcatg ttaattctaa tttaatattg gcacataaaa tatctgacta   13740
ttttcataat acttacattt taagtactaa tttagctgga cattggattc tgattataca   13800
acttatgaaa gattctaaag gtatttttga aaaagattgg ggagagggat atataactga   13860
tcatatgttt attaatttga agttttctt caatgcttat aagacctatc tcttgtgttt   13920
tcataaaggt tatggcaaag caaagctgga gtgtgatatg aacacttcag atcttctatg   13980
tgtattggaa ttaatagaca gtagttattg gaagtctatg tctaaggtat ttttagaaca   14040
aaaagttatc aaatacattc ttagccaaga tgcaagttta catagagtaa aaggatgtca   14100
tagcttcaaa ttatggtttc ttaaacgtct taatgtagca gaattcacag tttgcccttg   14160
ggttgttaac atagattatc atccaacaca tatgaaagca atattaactt atatagatct   14220
tgttagaatg ggattgataa atatagatag aatacacatt aaaaataaac acaaattcaa   14280
tgatgaattt tatacttcta atctcttcta cattaattat aacttctcag ataatactca   14340
tctattaact aaacatataa ggattgctaa ttctgaatta gaaaataatt acaacaaatt   14400
atatcatcct acaccagaaa ccctagagaa tatactagcc aatccgatta aagtaatga    14460 caaaagaca ctgaatgact attgtatagg taaaaatgtt gactcaataa tgttaccatt    14520
gttatctaat aagaagctta ttaaatcgtc tgcaatgatt agaaccaatt acagcaaaca   14580
agatttgtat aatttattcc ctatggttgt gattgataga attatagatc attcaggcaa   14640
tacagccaaa tccaaccaac tttacactac tacttcccac caaatatctt tagtgcacaa   14700
tagcacatca ctttactgca tgcttcctg gcatcatatt aatagattca attttgtatt   14760
```

```
tagttctaca ggttgtaaaa ttagtataga gtatatttta aaagatctta aaattaaaga    14820
tcccaattgt atagcattca taggtgaagg agcagggaat ttattattgc gtacagtagt    14880
ggaacttcat cctgacataa gatatattta cagaagtctg aaagattgca atgatcatag    14940
tttacctatt gagttttaa ggctgtacaa tggacatatc aacattgatt atggtgaaaa    15000
tttgaccatt cctgctacag atgcaaccaa caacattcat tggtcttatt tacatataaa    15060
gtttgctgaa cctatcagtc tttttgtctg tgatgccgaa ttgtctgtaa cagtcaactg    15120
gagtaaaatt ataatagaat ggagcaagca tgtaagaaag tgcaagtact gttcctcagt    15180
taataaatgt atgttaatag taaaatatca tgctcaagat gatattgatt tcaaattaga    15240
caatataact atattaaaaa cttatgtatg cttaggcagt aagttaaagg gatcggaggt    15300
ttacttagtc cttacaatag gtcctgcgaa tatattccca gtatttaatg tagtacaaaa    15360
tgctaaattg atactatcaa gaaccaaaaa tttcatcatg cctaagaaag ctgataaaga    15420
gtctattgat gcaaatatta aaagtttgat acccttctt tgttacccta taacaaaaaa    15480
aggaattaat actgcattgt caaaactaaa gagtgttgtt agtggagata tactatcata    15540
ttctatagct ggacgtaatg aagttttcag caataaactt ataaatcata agcatatgaa    15600
catcttaaaa tggttcaatc atgtttaaa tttcagatca acagaactaa actataacca    15660
tttatatatg gtagaatcta catatcctta cctaagtgaa ttgttaaaca gcttgacaac    15720
caatgaactt aaaaaactga ttaaaatcac aggtagtctg ttatacaact ttcataatga    15780
ataatgaata aagatcttat aataaaaatt cccatagcta tacactaaca ctgtattcaa    15840
ttatagttat taaaaattaa aaatcgtacg atttttttaa taacttttag tgaactaatc    15900
ctaaagttat cattttaatc ttggaggaat aaatttaaac cctaatctaa ttggtttata    15960
tgtgtattaa ctaaattacg agatattagt ttttgacact ttttttctcg tgggtcggca    16020
tggcatctcc acctcctcgc ggtccgacct gggcatccga aggaggacgc acgtccactc    16080
ggatggctaa gggagctgct aacaaagccc gaaggaagc tgagttggct gctgccaccg    16140
ctgagcaata actagcataa cccttgggg cctctaaacg ggtcttgagg ggttttttgc    16200
tgaaaggagg aactatatac gcgtaagctt ctcgacccat tctcatgttt gacagcttat    16260
catcgaattt ctgccattca tccgcttatt atcacttatt caggcgtagc aaccaggcgt    16320
ttaagggcac caataactgc cttaaaaaaa ttacgccccg ccctgccact catcgcagta    16380
ctgttgtaat tcattaagca ttctgccgac atggaagcca tcacagacgg catgatgaac    16440
ctgaatcgcc agcggcatca gcaccttgtc gccttgcgta taatatttgc ccatggtgaa    16500
aacgggggcg aagaagttgt ccatattggc cacgtttaaa tcaaaactgg tgaaactcac    16560
ccagggattg gctgagacga aaacatatt ctcaataaac cctttaggga ataggccag    16620 gtttccaccg taacacgcca catcttgcga atatatgtgt agaaactgcc ggaaatcgtc    16680
gtggtattca ctccagagcg atgaaaacgt ttcagtttgc tcatggaaaa cggtgtaaca    16740
agggtgaaca ctatcccata tcaccagctc accgtctttc attgccatac ggaattccgg    16800
atgagcattc atcaggcggg caagaatgtg aataaaggcc ggataaaact tgtgcttatt    16860
ttctcttacg gtctttaaaa aggccgtaat atccagctga acgtctggt tataggtaca    16920 ttgagcaact gactgaaatg cctcaaaatg ttctttacga tgccattggg atatatcaac    16980
ggtggtatat ccagtgattt ttttctccat tttagcttcc ttagctcctg aaaatctcga    17040
taactcaaaa aatacgcccg gtagtgatct tatttcatta tggtgaaagt tggaacctct    17100
tacgtgccga tcaacgtctc attttcgcca aaagttggcc cagggcttcc cggtatcaac    17160
```

```
agggacacca ggatttattt attctgcgaa gtgatcttcc gtcacaggta tttattcgcg   17220
ataagctcat ggagcggcgt aaccgtcgca caggaaggac agagaaagcg cggatctggg   17280
aagtgacgga cagaacggtc aggacctgga ttggggaggc ggttgccgcc gctgctgctg   17340
acggtgtgac gttctctgtt ccggtcacac cacatacgtt ccgccattcc tatgcgatgc   17400
acatgctgta tgccggtata ccgctgaaag ttctgcaaag cctgatggga cataagtcca   17460
tcagttcaac ggaagtctac acgaaggttt tgcgctgga tgtggctgcc cggcaccggg   17520
tgcagtttgc gatgccggag tctgatgcgg ttgcgatgct gaaacaatta tcctgagaat   17580
aaatgccttg gcctttatat ggaaatgtgg aactgagtgg atatgctgtt tttgtctgtt   17640
aaacagagaa gctggctgtt atccactgag aagcgaacga acagtcggg aaaatctccc    17700 attatcgtag agatccgcat tattaatctc aggagcctgt gtagcgttta taggaagtag   17760
tgttctgtca tgatgcctgc aagcggtaac gaaaacgatt tgaatatgcc ttcaggaaca   17820
atagaaatct tcgtgcggtg ttacgttgaa gtggagcgga ttatgtcagc aatggacaga   17880
acaacctaat gaacacagaa ccatgatgtg gtctgtcctt ttacagccag taggctcgcc   17940
gcagtcgagc gacggcgaag ccctcgagtg agcgaggaag caccagggaa cagcacttat   18000
atattctgct tacacacgat gcctgaaaaa acttcccttg gggttatcca cttatccacg   18060
gggatatttt tataattatt tttttttatag ttttttagatc ttcttttta gagcgccttg    18120 taggccttta tccatgctgg ttctagagaa ggtgttgtga caaattgccc tttcagtgtg   18180
acaaatcacc ctcaaatgac agtcctgtct gtgacaaatt gcccttaacc ctgtgacaaa   18240
ttgccctcag aagaagctgt ttttttcacaa agttatccct gcttattgac tcttttttat   18300
ttagtgtgac aatctaaaaa cttgtcacac ttcacatgga tctgtcatgg cggaaacagc   18360
ggttatcaat cacaagaaac gtaaaaatag cccgcgaatc gtccagtcaa cgacctcac    18420 tgaggcggca tatagtctct cccgggatca aaaacgtatg ctgtatctgt tcgttgacca   18480
gatcagaaaa tctgatggca ccctacagga acatgacggt atctgcgaga tccatgttgc   18540
taaatatgct gaaatattcg gattgacctc tgcggaagcc agtaaggata tacggcaggc   18600
attgaagagt ttcgcgggga aggaagtggt tttttatcgc cctgaagagg atgccggcga   18660 tgaaaaggc tatgaatctt ttccttggtt tatcaaacgt gcgcacagtc catccagagg   18720
gctttacagt gtacatatca acccatatct cattcccttc tttatcgggt tacagaaccg   18780
gtttacgcag tttcggctta gtgaaacaaa agaaatcacc aatccgtatg ccatgcgttt   18840
atacgaatcc ctgtgtcagt atcgtaagcc ggatggctca ggcatcgtct ctctgaaaat   18900
cgactggatc atagagcgtt accagctgcc tcaaagttac cagcgtatgc ctgacttccg   18960
ccgccgcttc ctgcaggtct gtgttaatga gatcaacagc agaactccaa tgcgcctctc   19020
atacattgag aaaaagaaag gccgccagac gactcatatc gtattttcct tccgcgatat   19080
cacttccatg acgacaggat agtctgaggg ttatctgtca cagatttgag ggtggttcgt   19140
cacatttgtt ctgacctact gagggtaatt tgtcacagtt ttgctgtttc cttcagcctg   19200
catggatttt ctcatacttt ttgaactgta atttttaagg aagccaaatt tgagggcagt   19260
ttgtcacagt tgatttcctt ctctttccct tcgtcatgtg acctgatatc gggggttagt   19320
tcgtcatcat tgatgagggt tgattatcac agtttattac tctgaattgg ctatccgcgt   19380
gtgtacctct acctggagtt tttcccacgt tggatatttc ttcttgcgct gagcgtaaga   19440
gctatctgac agaacagttc ttctttgctt cctcgccagt tcgctcgcta tgctcggtta   19500
```

-continued

```
cacggctgcg gcgagcgcta gtgataataa gtgactgagg tatgtgctct tcttatctcc   19560
ttttgtagtg ttgctcttat tttaaacaac tttgcggttt tttgatgact ttgcgatttt   19620
gttgttgctt tgcagtaaat tgcaagattt aataaaaaaa cgcaaagcaa tgattaaagg   19680
atgttcagaa tgaaactcat ggaaacactt aaccagtgca taaacgctgg tcatgaaatg   19740
acgaaggcta tcgccattgc acagtttaat gatgacagcc cggaagcgag gaaaataacc   19800
cggcgctgga gataggtga agcagcggat ttagttgggg tttcttctca ggctatcaga   19860
gatgccgaga aagcagggcg actaccgcac ccggatatgg aaattcgagg acgggttgag   19920
caacgtgttg gttatacaat tgaacaaatt aatcatatgc gtgatgtgtt tggtacgcga   19980
ttgcgacgtg ctgaagacgt atttccaccg gtgatcgggg ttgctgccca taaaggtggc   20040
gtttacaaaa cctcagtttc tgttcatctt gctcaggatc tggctctgaa ggggctacgt   20100
gttttgctcg tggaaggtaa cgaccccag ggaacagcct caatgtatca cggatgggta   20160
ccagatcttc atattcatgc agaagacact ctcctgcctt tctatcttgg ggaaaaggac   20220
gatgtcactt atgcaataaa gcccacttgc tggccggggc ttgacattat tccttcctgt   20280
ctggctctgc accgtattga aactgagtta atgggcaaat ttgatgaagg taaactgccc   20340
accgatccac acctgatgct ccgactggcc attgaaactg ttgctcatga ctatgatgtc   20400
atagttattg acagcgcgcc taacctgggt atcggcacga ttaatgtcgt atgtgctgct   20460
gatgtgctga ttgttcccac gcctgctgag ttgtttgact acacctccgc actgcagttt   20520
ttcgatatgc ttcgtgatct gctcaagaac gttgatctta aagggttcga gcctgatgta   20580
cgtattttgc ttaccaaata cagcaatagt aatggctctc agtccccgtg gatggaggag   20640
caaattcggg atgcctgggg aagcatggtt ctaaaaaatg ttgtacgtga acggatgaa   20700 gttggtaaag gtcagatccg gatgagaact gttttttgaac aggccattga tcaacgctct   20760
tcaactggtg cctggagaaa tgctctttct atttgggaac ctgtctgcaa tgaaatttc   20820 gatcgtctga ttaaaccacg ctgggagatt agataatgaa gcgtgcgcct gttattccaa   20880
aacatacgct caatactcaa ccggttgaag atacttcgtt atcgacacca gctgccccga   20940
tggtggattc gttaattgcg cgcgtaggag taatggctcg cggtaatgcc attactttgc   21000
ctgtatgtgg tcgggatgtg aagtttactc ttgaagtgct ccggggtgat agtgttgaga   21060
agacctctcg ggtatggtca ggtaatgaac gtgaccagga gctgcttact gaggacgcac   21120
tggatgatct catcccttct tttctactga ctggtcaaca gacaccggcg ttcggtcgaa   21180
gagtatctgg tgtcatagaa attgccgatg ggagtcgccg tcgtaaagct gctgcactta   21240
ccgaaagtga ttatcgtgtt ctggttggcg agctggatga tgagcagatg gctgcattat   21300
ccagattggg taacgattat cgcccaacaa gtgcttatga acgtggtcag cgttatgcaa   21360
gccgattgca gaatgaattt gctggaaata tttctgcgct ggctgatgcg gaaaatattt   21420
cacgtaagat tattacccgc tgtatcaaca ccgccaaatt gcctaaatca gttgttgctc   21480
ttttttctca ccccggtgaa ctatctgccc ggtcaggtga tgcacttcaa aaagccttta   21540
cagataaaga ggaattactt aagcagcagg catctaacct tcatgagcag aaaaaagctg   21600
gggtgatatt tgaagctgaa gaagttatca ctcttttaac ttctgtgctt aaaacgtcat   21660
ctgcatcaag aactagttta agctcacgac atcagtttgc tcctggagcg acagtattgt   21720
ataagggcga taaaatggtg cttaacctgg acaggtctcg tgttccaact gagtgtatag   21780
agaaaattga ggccattctt aaggaacttg aaaagccagc accctgatgc gaccacgttt   21840
tagtctacgt ttatctgtct ttacttaatg tccttttgtta caggccagaa agcataactg   21900
```

```
gcctgaatat tctctctggg cccactgttc cacttgtatc gtcggtctga taatcagact  21960
gggaccacgg tcccactcgt atcgtcggtc tgattattag tctgggacca cggtcccact  22020
cgtatcgtcg gtctgattat tagtctggga ccacggtccc actcgtatcg tcggtctgat  22080
aatcagactg ggaccacggt cccactcgta tcgtcggtct gattattagt ctgggaccat  22140
ggtcccactc gtatcgtcgg tctgattatt agtctgggac cacggtccca ctcgtatcgt  22200
cggtctgatt attagtctgg aaccacggtc ccactcgtat cgtcggtctg attattagtc  22260
tgggaccacg gtcccactcg tatcgtcggt ctgattatta gtctgggacc acgatcccac  22320
tcgtgttgtc ggtctgatta tcggtctggg accacggtcc cacttgtatt gtcgatcaga  22380
ctatcagcgt gagactacga ttccatcaat gcctgtcaag ggcaagtatt gacatgtcgt  22440
cgtaacctgt agaacggagt aacctcggtg tgcggttgta tgcctgctgt ggattgctgc  22500
tgtgtcctgc ttatccacaa catttgcgc acggttatgt ggacaaaata cctggttacc  22560
caggccgtgc cggcacgtta accgggctgc atccgatgca agtgtgtcgc tgtcgagttt  22620
```

RESPIRATORY SYNCYTIAL VIRUS EXPRESSION VECTORS

CROSS REFERENCE TO RELATED APPLICATIONS

This application is a division of U.S. application Ser. No. 13/444,338 filed Apr. 11, 2012, which claims the benefit of U.S. Provisional Application No. 61/474,365 filed Apr. 12, 2011. The entirety of each of these applications is hereby incorporated by reference for all purposes.

STATEMENT REGARDING FEDERALLY SPONSORED RESEARCH OR DEVELOPMENT

This invention was made with government support under RR025008 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 11064USDIV_ST25.txt. The text file is 51 KB, was created on Jan. 16, 2019, and is being submitted electronically via EFS-Web.

BACKGROUND

Human respiratory syncytial virus (RSV) causes respiratory tract infections. It is the major cause of hospital visits during infancy and childhood. After translation of viral mRNAs, a full-length (+) antigenomic RNA is produced as a template for replication of the (−) RNA genome. Infectious recombinant RSV (rRSV) particles may be recovered from transfected plasmids. Co-expression of RSV N, P, L, and M2-1 proteins as well as the full-length antigenomic RNA is sufficient for RSV replication. See Collins et al., Proc Natl Acad Sci USA., 1995, 92(25):11563-11567 and U.S. Pat. No. 6,790,449.

Despite the existence of methods of generating RSV particles from cloned cDNA, stability of RSV cDNA remains a challenge. A region of the RSV small hydrophobic protein (SH) gene is unstable as cloned cDNA. See e.g., Skiadopoulos et al., Virology 345, 492-501 (2006). Investigators have suffered failures in cloning RSV cDNA in plasmids, despite extensive experience with other viruses and cDNA cloning. Labs typically use a RSV antigenomic cDNA cloned in the plasmid pBR322. In order to maintain the antigenomic cDNA in this plasmid, one typically grows the bacteria at 30° C. and low aeration. Nevertheless, plasmids frequently undergo rearrangements and clone loss. Taken together, plasmid stability is a factor limiting progress in RSV research and vaccine development. Thus, there is a need to identify improved methods of generating RSV.

One may recover viruses from bacterial artificial chromosome (BAC) vectors. See Roth et al., Vet Res., 2011, 42(1):3 and Alder et al., Rev Med Virol., 2003, 13(2):111-21 and U.S. Pat. No. 7,892,822. BAC recombineering refers to a method of introducing mutations in cDNAs cloned in a BAC vectors via homologous recombination in *E. coli*. A BAC recombineering system based on selection and counter-selection of the galK operon was disclosed by Warming et al, Nucleic Acids Research, 2005, 33, e36. References cited herein are not an admission of prior art.

SUMMARY

In certain embodiments, the disclosure relates to vectors comprising a bacterial artificial chromosome (BAC), and a nucleic acid sequence comprising a paramyxovirus genome, antigenome, or gene of a paramyxovirus. Typically, the paramyxovirus is respiratory syncytial virus (RSV), human metapneumovirus, nipah virus, hendra virus, or pneumonia virus and the BAC contains all genes that are essential for the generation of an infectious viral particle in a host cell. The nucleic acid sequence may be a viral genome or antigenome in operable combination with a regulatory element. Typically, the bacterial artificial chromosome comprises one or more genes selected from the group consisting of oriS, repE, parA, and parB genes of Factor F in operable combination with a selectable marker, e.g., a gene that provides resistance to an antibiotic.

The nucleic acid sequence may be the genomic or antigenomic sequence of the virus which is optionally mutated, e.g., RSV strain which is optionally mutated. In certain embodiments, the expression vector is a plasmid comprising MluI, ClaI, BstBI, SacI restriction endonuclease cleavage sites and optionally an AvrII restriction endonuclease cleavage site outside the region of the wild-type viral sequence or outside the sequences that encode viral genes or outside the viral genome or antigenome. In certain embodiments, the nucleic acid sequence further comprises a selectable marker or reporter gene in operable combination therewith, e.g., a gene that encodes a fluorescent protein.

In certain embodiments, the disclosure relates to isolated bacteria comprising one or more vectors disclosed herein, and other embodiments, the disclosure relates to an isolated cell comprising one or more vectors disclosed herein. In certain embodiments, the vector comprises an RSV antigenome and one or more vectors selected from the group consisting of: a vector encoding an N protein of RSV, a vector encoding a P protein of RSV, a vector encoding an L protein of RSV, and a vector encoding an M2-1 protein of RSV. Typically, the vector comprises a regulatory element, e.g., promoter, and the isolated eukaryotic cell expresses a nucleic acid or polypeptide that activates the regulatory element, e.g., encodes a polypeptide that activates transcription downstream of the promoter. In certain embodiments, the promoter is T7, and the polypeptide that activates transcription downstream of the promoter is T7 RNA polymerase.

In certain embodiments, the disclosure relates to methods of generating respiratory syncytial virus (RSV) particles comprising inserting a vector with a BAC gene and a RSV antigenome into an isolated eukaryotic cell and inserting one or more vectors selected from the group consisting of: a vector encoding an N protein of RSV, a vector encoding a P protein of RSV, a vector encoding an L protein of RSV, and a vector encoding an M2-1 protein of RSV into the cell under conditions such that RSV particle is formed. Inserting a vector into a cell may occur by physically injecting, electroporating, or mixing the cell and the vector under conditions such that the vector infects the cell.

In certain embodiments, the disclosure relates to a non-naturally occurring isolated nucleic acid comprising or consisting essential of SEQ ID NO: 1, SEQ ID NO: 2, or SEQ ID NO: 3 or a sequence with substantial identity.

In certain embodiments, the disclosure relates to a non-naturally occurring isolated nucleic acid comprising or consisting essential of SEQ ID NO: 4 and SEQ ID NO: 5 or a sequence with substantial identity.

In certain embodiments, the disclosure relates to a recombinant vector comprising a bacterial artificial chromosome, a nucleic acid sequence comprising SEQ ID NO: 4 or a sequence with substantial identity; and a nucleic acid sequence comprising SEQ ID NO: 5 or a sequence with substantial identity.

In certain embodiment, the disclosure relates to processes of producing a recombinant vector comprising a bacterial artificial chromosome and SacI, ClaI and AvrII restriction endonuclease cleavage sites comprising mixing a nucleic acid comprising a bacterial artificial chromosome and a nucleic acid comprising SacI, ClaI and AvrII restriction endonuclease cleavage sites under conditions such that a continuous nucleic acid comprising a bacterial artificial chromosome and a SacI, ClaI and AvrII restriction endonuclease cleavage sites is formed.

In certain embodiments, the disclosure relates to a recombinant vector comprising SEQ ID NO: 6 or a sequence with substantial identity.

BRIEF DESCRIPTION OF THE DRAWINGS

Figure 3E:
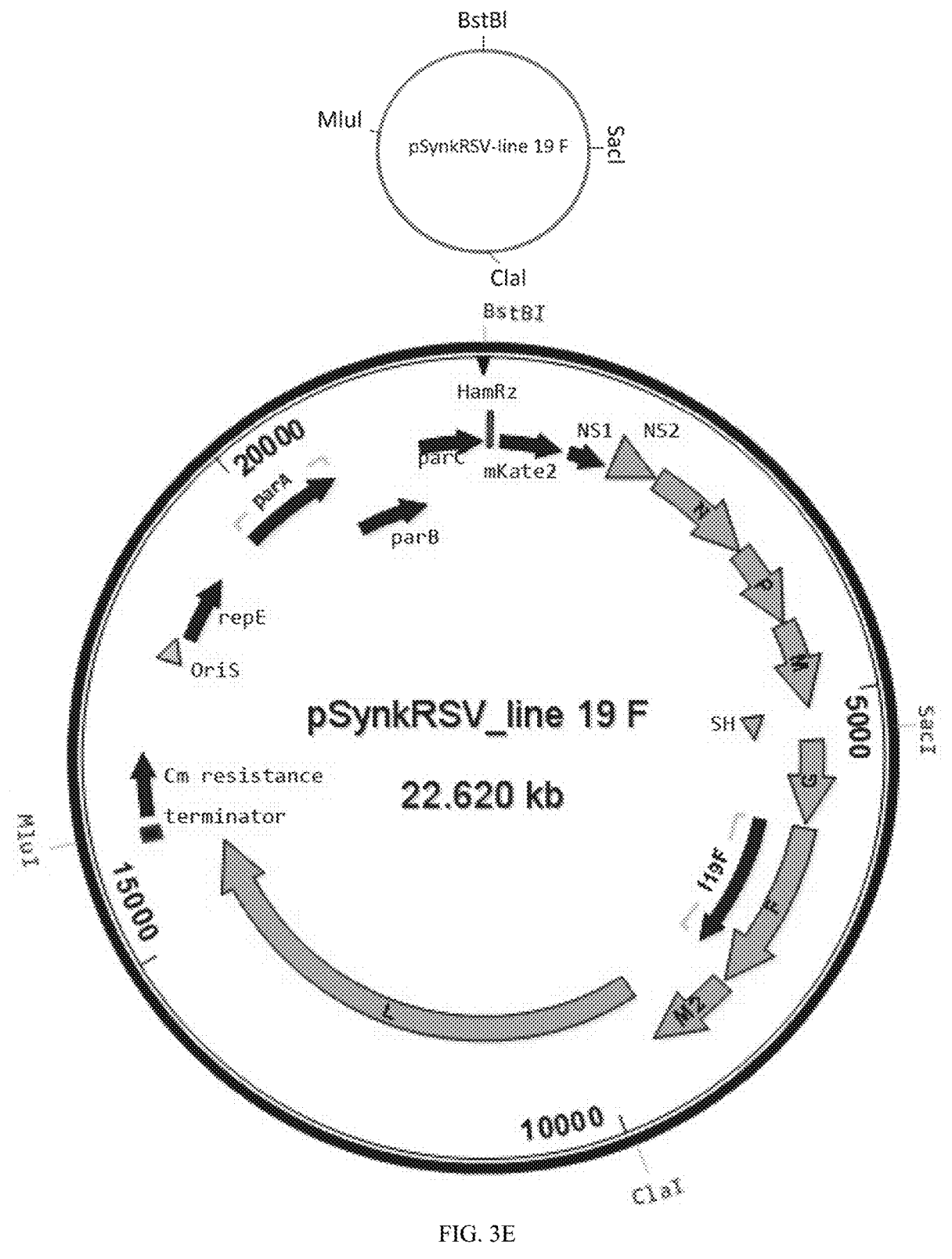

FIG. 3E shows recombineering is used to delete nucleotides between two ClaI sites generating pSynRSV-line 19F.

DETAILED DESCRIPTION

Figure 1:
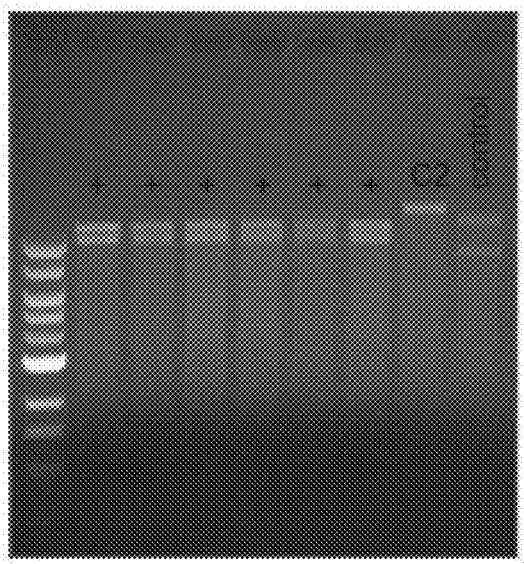
FIG. 1 shows a gel after insertion of galK operon into BAC-RSV by recombineering. MluI digest. Lane 1, ladder marker. Mini-prep BAC DNAs (lanes 2 to 7). Lane 8, parental BAC-RSV "C2" clone. Lane 9, galK-containing plasmid. galK operon has a Mlu I restriction site that serves as a marker for introduction of galK by homologous recombination.
Figure 2:
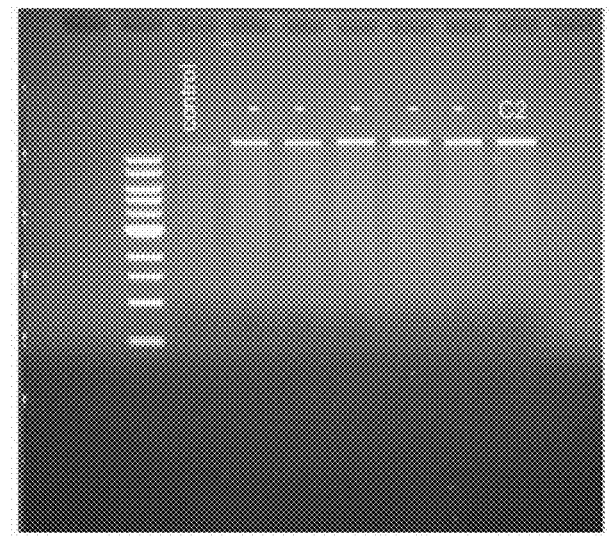
FIG. 2 shows a gel after deletion of galK operon from BAC-RSV by recombineering. MluI digest of galK-containing plasmid (lane 2), BAC mini-prep DNAs (lanes 3-7), and parental BAC-RSV clone C2 (lane 8).
Figure 3A:
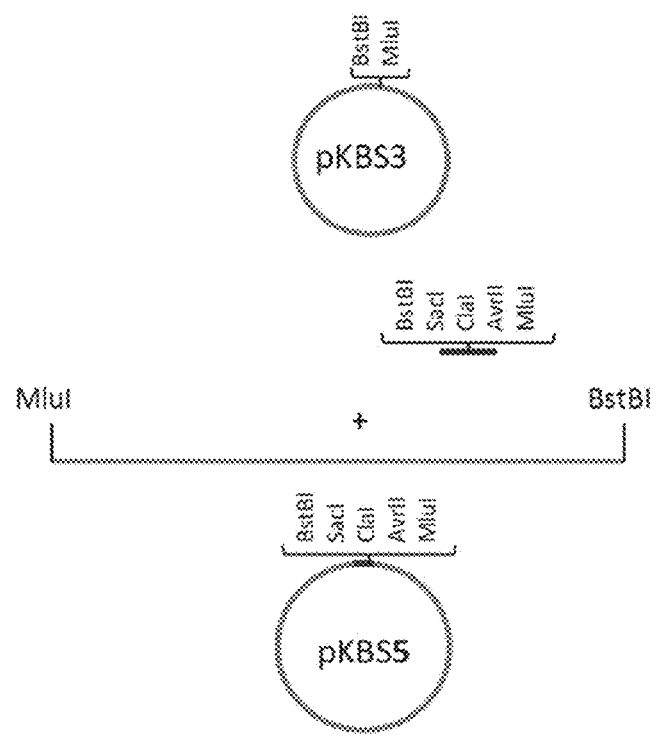
FIG. 3A schematically illustrate steps for creating a BAC-RSV. Three plasmids with RSV segments are generated (see experimental). pKBS3 is cut at BstBI and MluI sites to linearize and is ligated to an oligonucleotide adapter providing pKBS5.
Figure 3B:
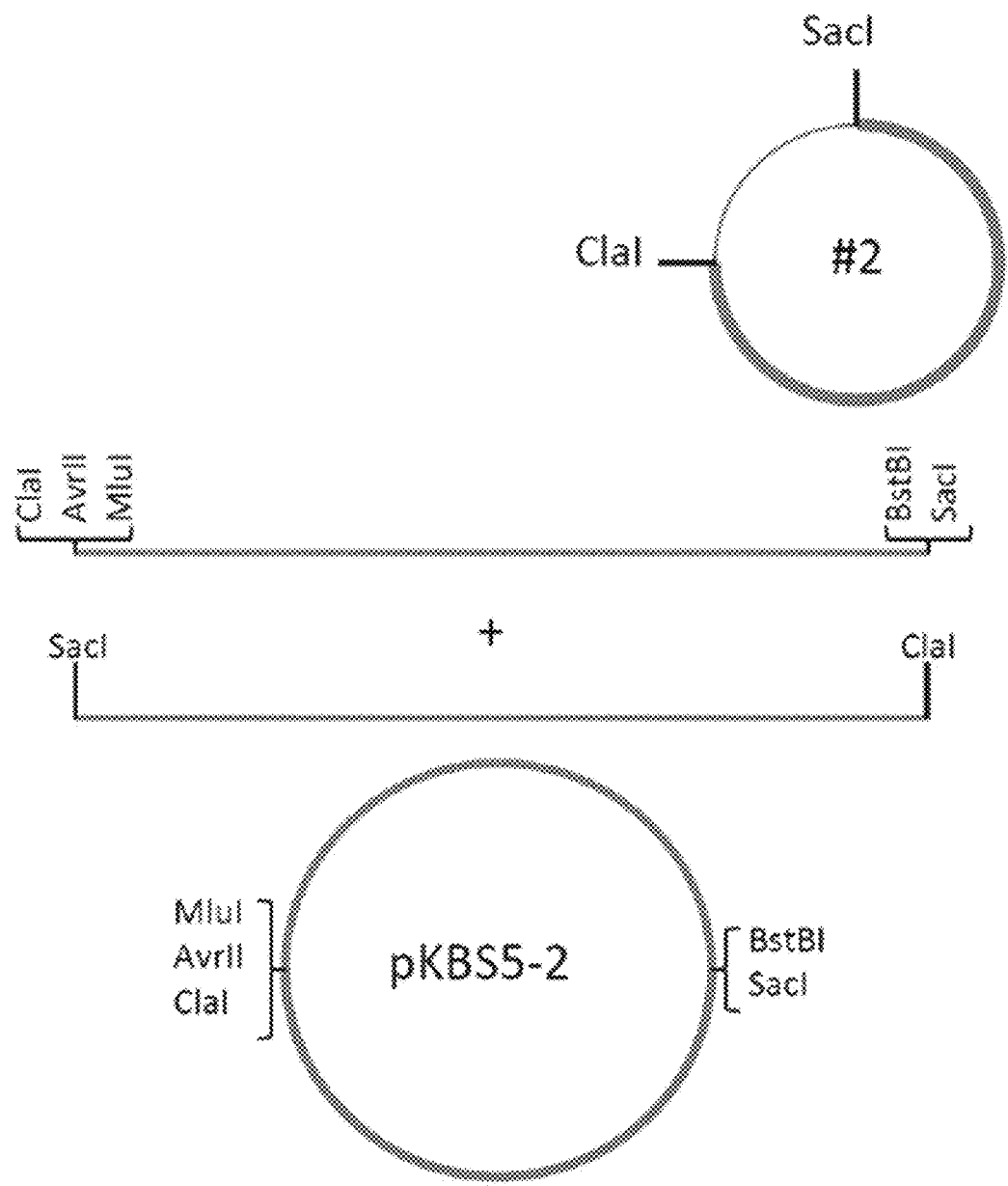
FIG. 3B shows pSynRSV #2 with SacI and ClaI is cut and ligated to pKBS5 providing pKBS5-2.
Figure 3C:
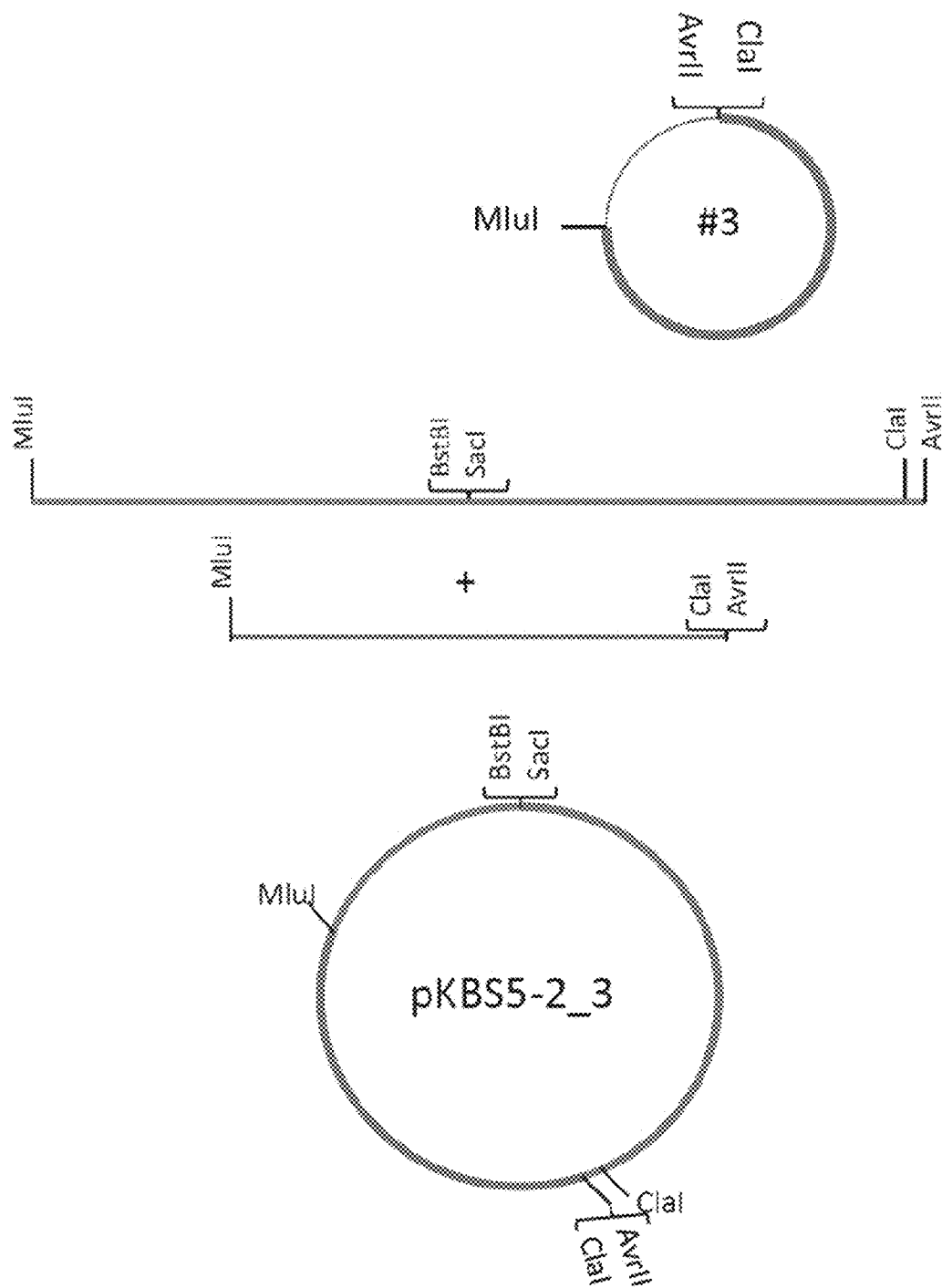
FIG. 3C shows pSynRSV #3 with AvrII and MluI is cut and ligated to pKBS5_2 providing pKBS5_2_3.
Figure 3D:
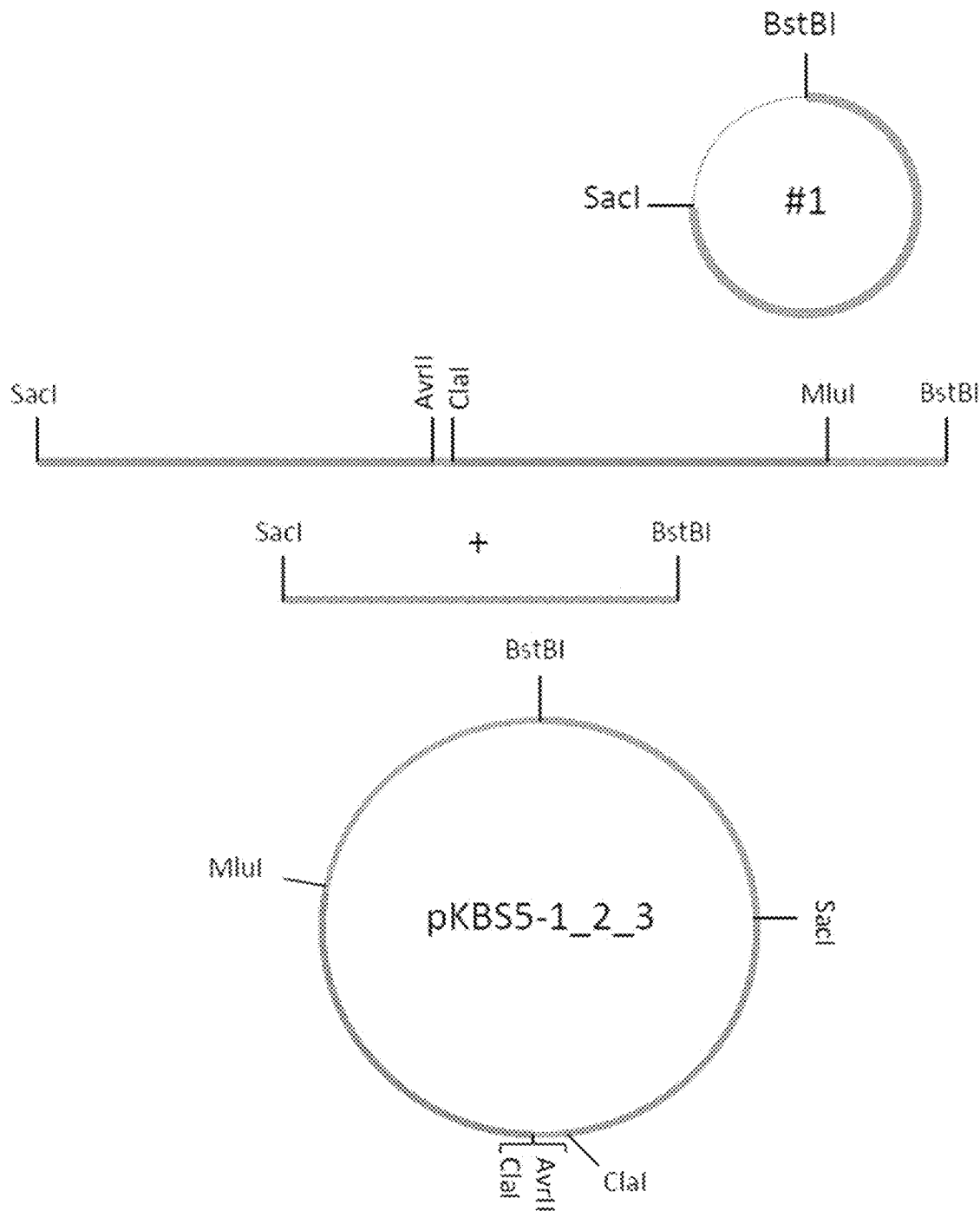
FIG. 3D shows pSynRSV #1 with BstBI and SacI is cut and ligated to pKBS5_2_3 providing pKBS5_1_2_3.

It has been discovered that cultivating RSV in *E. coli* bacteria may be accomplished by utilizing a plasmid containing a bacterial artificial chromosome. A plasmid comprising a bacterial artificial chromosome is disclosed that contains the complete antigenomic sequence of respiratory syncytial virus (RSV) strain A2 except the F gene, which is the antigenomic sequence of RSV strain line 19. Along with helper plasmids, it can be used in the reverse genetics system for the recovery of infectious virus. The antigenome sequence on the plasmid can be mutated prior to virus recovery to generate viruses with desired mutations.

The plasmid is an improvement on current RSV antigenomic plasmids for several reasons. Each RSV gene is flanked by restriction endonuclease cleavage sites to allow for easy manipulation of any gene. As a basis for viral mutagenesis, this plasmid may be used to design attenuated viruses for use in vaccines. An extra gene encoding the modified Katushka, mKate2, protein has been included in the antigenome prior to the first RSV gene. Katushka is a red fluorescent protein which would be expressed in concert with the other RSV genes and would serve as visual evidence of virus replication. Changes have also been made to the ribozyme sequences that flank the RSV antigenome and play a role in the production of infectious virus through reverse genetics.

The disclosed vectors allow for efficient mutagenesis through recombineering. This mutagenesis method requires little to no ligation cloning but relies on the recombination machinery present in bacteria harboring certain genes from a bacteriophage. Because RSV genes are often unstable in bacteria predominantly used for cloning, such as *Escherichia coli* (*E. coli*), it is believed that the single digit copy nature of the bacterial artificial chromosome avoids the trouble with instability.

Respiratory Syncytial Virus (RSV)

Typically, the RSV particle contains a viral genome within a helical nucleocapsid which is surrounded by matrix proteins and an envelope containing glycoproteins. The genome of human wild-type RSV encodes the proteins, NS1, NS2, N, P, M, SH, G, F, M2-1, M2-2, and L. G, F, and SH are glycoproteins. The F gene has been incorporated into a number of viral vaccines. RSV polymerase activity consists of the large protein (L) and phosphoprotein (P). The viral M2-1 protein is used during transcription and is likely to be a component of the transcriptase complex. The viral N protein is used to encapsidate the nascent RNA during replication.

The genome is transcribed and replicated in the cytoplasm of a host cell. Host-cell transcription typically results in synthesis of ten methylated and polyadenylated mRNAs. The antigenome is positive-sense RNA complement of the genome produced during replication, which in turn acts as a template for genome synthesis. The viral genes are flanked by conserved gene-start (GS) and gene-end (GE) sequences. At the 3' and 5' ends of the genome are leader and trailer nucleotides. The wild type leader sequence contains a promoter at the 3' end. When the viral polymerase reaches a GE signal, the polymerase polyadenylates and releases the mRNA and reinitiates RNA synthesis at the next GS signal. The L-P complex is believed to be responsible for recognition of the promoter, RNA synthesis, capping and methylation of the 5' termini of the mRNAs and polyadenylation of their 3' ends. It is believed that the polymerase sometimes dissociates from the gene at the junctions. Because the polymerase initiates transcription at the 3' end of the genome, this results in a gradient of expression, with the genes at the 3' end of the genome being transcribed more frequently than those at the 5' end.

To replicate the genome, the polymerase does not respond to the cis-acting GE and GS signals and generates positive-sense RNA complement of the genome, the antigenome. At the 3' end of the antigenome is the complement of the trailer, which contains a promoter. The polymerase uses this promoter to generate genome-sense RNA. Unlike mRNA, which is released as naked RNA, the antigenome and genome RNAs are encapsidated with virus nucleoprotein (N) as they are synthesized.

Reference to chimeric RSV is contemplated to include certain mutations, deletions, or variant combinations, such as cold-passaged (cp) non-temperature sensitive (ts) derivatives of RSV, cpRSV, such as rA2cp248/404/1030ΔSH.

rA2cp248/404ΔSH contains 4 independent attenuating genetic elements: cp which is based on 5 missense mutations in the N and L proteins and the F glycoprotein that together confer the non-ts attenuation phenotype of cpRSV; ts248, a missense mutation in the L protein; ts404, a nucleotide substitution in the gene-start transcription signal of the M2 gene; and ΔSH, complete deletion of the SH gene. rA2cp248/404/1030ΔSH contains 5 independent attenuating genetic elements: those present in rA2cp248/404ΔSH and ts1030, another missense mutation in the L protein. See Karron et al., J Infect Dis., 2005, 191(7): 1093-1104, hereby incorporated by reference. Within certain embodiments, it is contemplated that the RSV antigenome may contain deletion or mutations in nonessential genes (e.g., the SH, NS1, NS2, and M2-2 genes) or combinations thereof.

It is contemplated that the nucleic acid may contain a viral genome other than RSV which includes an F gene of RSV such as live-attenuated vaccines, e.g., sendai virus (a murine parainfluenza virus) based vaccine or a live-attenuated chimeric bovine/human with human parainfluenza virus vaccine, genetically engineered to express human RSV F protein.

Bacterial Artificial Chromosomes (BACs)

In certain embodiments, the disclosure relates to vectors and nucleic acids that contain bacterial artificial chromosomes. A bacterial cloning system for mapping and analysis of complex genomes has been disclosed in Shizuya et al., Proc. Natl. Acad. Sci., 1992, 89:8794-8797. The BAC system (for bacterial artificial chromosome) is based on *Escherichia coli* and its single-copy plasmid F factor which were described as useful for cloning large fragments of human DNA. The F factor encodes for genes that regulate its own replication including oriS, repE, parA, and parB. The oriS and repE genes mediate the unidirectional replication of the F factor while parA and parB typically maintain copy number at a level of one or two per *E. coli* genome. It is contemplated that the genes and the chromosome may contain mutations, deletions, or variants with desired functional attributes. The BAC vector (pBAC) typically contains these genes as well as a resistance marker and a cloning segment containing promotors for incorporating nucleic acid segments of interest by ligating into restriction enzyme sites. Exemplary BAC systems include those described in Shizuya & Kouros-Hehr, Keio J Med, 2001, 50(1): 26-30, hereby incorporated by reference.

One may reconstitute infectious RSV virus from the RSV BAC plasmids disclosed herein. BAC vectors can be transfected to bacteria such as *E. coli* by electroporation. The RSV-BACs disclosed herein may be stably maintained in bacteria, re-isolated from the bacteria, and inserted into a eukaryotic cell along with one or more vectors that express the N, P, L, and M2-1 proteins. These cells produce infective RSV particles. Production of infectious RSV results from co-transfection of plasmids encoding N, P, L, and M2-1 proteins and the antigenome under control of the T7 promoter into BHK-21 cells that express T7 RNA polymerase (BSR cells). See Buchholz et al., J Virol., 2000, 74(3):1187-1199, hereby incorporated by reference.

Vaccines

A number of attenuated RSV strains as candidate vaccines for intranasal administration have been developed using multiple rounds of chemical mutagenesis to introduce multiple mutations into a virus. Evaluation in rodents, chimpanzees, adults and infants indicate that certain of these candidate vaccine strains are immunogenic and may be attenuated. Nucleotide sequence analysis of some of these attenuated viruses indicates that each level of increased attenuation is typically associated with two or more new nucleotide and amino acid substitutions.

The disclosure provides the ability to distinguish between silent incidental mutations versus those responsible for phenotype differences by introducing the mutations, separately and in various combinations, into the genome or antigenome of infectious wild-type RSV. This process identifies mutations responsible for phenotypes such as attenuation, temperature sensitivity, cold-adaptation, small plaque size, host range restriction, etc. Mutations from this menu can then be introduced in various combinations to calibrate a vaccine virus to an appropriate level of attenuation, etc., as desired. Moreover, the present disclosure provides the ability to combine mutations from different strains of virus into one strain.

The present disclosure also provides for methods of attenuation. For example, individual internal genes of human RSV can be replaced with their bovine, murine or other RSV counterpart. This may include part or all of one or more of the NS1, NS2, N, P, M, SH, M2-1, M2-2 and L genes, or parts of the G and F genes. Reciprocally, means are provided to generate a live attenuated bovine RSV by inserting human attenuating genes into a bovine RSV genome or antigenome background. Human RSV bearing bovine RSV glycoproteins provides a host range restriction favorable for human vaccine preparations. Bovine RSV sequences which can be used in the present disclosure are described in, e.g., Pastey et al., J. Gen. Viol. 76:193-197 (1993); Pastey et al., Virus Res. 29:195-202 (1993); Zamora et al., J. Gen. Virol. 73:737-741 (1992); Mallipeddi et al., J. Gen. Virol. 74:2001-2004 (1993); Mallipeddi et al., J. Gen. Virol. 73:2441-2444 (1992); and Zamora et al., Virus Res. 24:115-121 (1992), each of which is incorporated herein by reference.

The disclosure also provides the ability to analyze other types of attenuating mutation and to incorporate them into infectious RSV for vaccine or other uses. For example, a tissue culture-adapted nonpathogenic strain of pneumonia virus of mice (the murine counterpart of RSV) lacks a cytoplasmic tail of the G protein (Randhawa et al., Virology 207: 240-245 (1995)). By analogy, the cytoplasmic and transmembrane domains of each of the RSV glycoproteins, F, G and SH, can be deleted or modified to achieve attenuation.

Other mutations for use in infectious RSV of the present disclosure include mutations in cis-acting signals identified during mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Other mutations involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986), incorporated herein by reference) can be shortened or lengthened or changed in sequence content, and the naturally-occurring gene overlap (Collins et al., Proc. Natl. Acad. Sci. USA 84:5134-5138 (1987), incorporated herein by reference) can be removed or changed to a different intergenic region by the methods described herein.

In another embodiment, RSV useful in a vaccine formulation can be conveniently modified to accommodate antigenic drift in circulating virus. Typically, the modification will be in the G and/or F proteins. The entire G or F gene, or the segment(s) encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B would broaden the response to cover a wider spectrum of the relatively diverse subgroup A and B strains present in the human population.

An infectious RSV clone of the disclosure can also be engineered to enhance its immunogenicity and induce a level of protection greater than that provided by natural infection, or vice versa, to identify and ablate epitopes associated with undesirable immunopathologic reactions. Enhanced immunogenicity of the vaccines produced by the present disclosure addresses one of the greatest obstacles to controlling RSV, namely the incomplete nature of immunity induced by natural infection. An additional gene may be inserted into or proximate to the RSV genome or antigenome which is under the control of an independent set of transcription signals. Genes of interest include those encoding cytokines (e.g., IL-2 through IL-15, especially IL-3, IL-6 and IL-7, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

For vaccine use, virus produced according to the present disclosure can be used directly in vaccine formulations, or lyophilized, as desired, using lyophilization protocols well known to the artisan. Lyophilized virus will typically be maintained at about 4 degrees C. When ready for use the lyophilized virus is reconstituted in a stabilizing solution, e.g., saline or comprising SPG, Mg, and HEPES, with or without adjuvant, as further described below.

Thus, RSV vaccines of the disclosure contain as an active ingredient an immunogenetically effective amount of RSV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a RSV composition as described herein, via aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV infection, particularly of the lower respiratory tract.

The host to which the vaccine are administered can be any mammal which is susceptible to infection by RSV or a closely related virus and which host is capable of generating a protective immune response to the antigens of the vaccinizing strain. Thus, suitable hosts include humans, non-human primates, bovine, equine, swine, ovine, caprine, lagomorph, rodents, etc. Accordingly, the invention provides methods for creating vaccines for a variety of human and veterinary uses.

The vaccine compositions containing the RSV of the disclosure are administered to a host susceptible to or otherwise at risk of RSV infection to enhance the host's own immune response capabilities. Such an amount is defined to be an "immunogenically effective dose." In this use, the precise amounts again depend on the host's state of health and weight, the mode of administration, the nature of the formulation. The vaccine formulations should provide a quantity of modified RSV of the invention sufficient to effectively protect the host patient against serious or life-threatening RSV infection.

The RSV produced in accordance with the present invention can be combined with viruses of the other subgroup or strains to achieve protection against multiple RSV subgroups or strains, or protective epitopes of these strains can be engineered into one virus as described herein. Typically, the different viruses will be in admixture and administered simultaneously but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

In some instances, it may be desirable to combine the RSV vaccines of the disclosure with vaccines which induce protective responses to other agents, particularly other childhood viruses. For example, the RSV vaccine of the present disclosure can be administered simultaneously with parainfluenza virus vaccine, such as described in Clements et al., J. Clin. Microbiol. 29:1175-1182 (1991), incorporated herein by reference. In another aspect of the disclosure the RSV can be employed as a vector for protective antigens of other respiratory tract pathogens, such as parainfluenza, by incorporating the sequences encoding those protective antigens into the RSV genome or antigenome which is used to produce infectious RSV as described herein.

Single or multiple administrations of the vaccine compositions of the disclosure can be carried out. In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses.

Levels of induced immunity can be monitored by measuring amounts of neutralizing secretory and serum antibodies, and dosages adjusted or vaccinations repeated as necessary to maintain desired levels of protection. Further, different vaccine viruses may be advantageous for different recipient groups. For example, an engineered RSV strain expressing an additional protein rich in T cell epitopes may be particularly advantageous for adults rather than for infants.

In yet another aspect of the disclosure, the RSV is employed as a vector for transient gene therapy of the respiratory tract. According to this embodiment, the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2-1 proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

Terms

The terms "protein" and "polypeptide" refer to compounds comprising amino acids joined via peptide bonds and are used interchangeably.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous gene" refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

The term "a polynucleotide having a nucleotide sequence encoding a gene" or "a polynucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25 50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (i.e., it is the complement of) the single-stranded nucleic acid sequence under conditions of low to high stringency as described above.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue.

In contrast, a "regulatable" or "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

Efficient expression of recombinant DNA sequences in eukaryotic cells typically requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation.

The term "vector" refers to nucleic acid molecules that transfer DNA segment(s) from one cell to another. The term "vehicle" is sometimes used interchangeably with "vector."

The terms "expression vector" or "expression cassette" refer to a recombinant nucleic acid containing a desired coding sequence and appropriate nucleic acid sequences used for the expression of the operably linked coding sequence in a particular host organism. Nucleic acid sequences used for expression in prokaryotes typically include a promoter, an operator (optional), and a ribosome binding site, often along with other sequences. Eukaryotic cells are known to utilize promoters, enhancers, and termination and polyadenylation signals.

The term "host cell" refers to any cell capable of replicating and/or transcribing and/or translating a heterologous gene. Thus, a "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of ganciclovir or acyclovir is cytotoxic; thus, growth of cells in selective medium containing ganciclovir or acyclovir selects against cells capable of expressing a functional HSV TK enzyme.

The term "reporter gene" refers to a gene encoding a protein that may be assayed. Examples of reporter genes include, but are not limited to, modified katushka, mkate and mkate2 (See, e.g., Merzlyak et al., Nat. Methods, 2007, 4, 555-557 and Shcherbo et al., Biochem. J., 2008, 418, 567-574), luciferase (See, e.g., deWet et al., Mol. Cell. Biol. 7:725 (1987) and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from ClonTech Laboratories, Palo Alto, Calif.), chloramphenicol acetyltransferase, beta-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" or "antigenome" refers to a nucleotide sequence whose sequence of nucleotide residues is in reverse 5' to 3' orientation in relation to the sequence of nucleotide residues in a sense strand. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex.

EXPERIMENTAL

Example 1: Expression of RSV in Plasmid Designed for Low Copy Number

Infectious recombinant RSV (rRSV) can be recovered from transfected plasmids. Co-expression of RSV N, P, L, and M2 1 proteins as well as the full-length antigenomic RNA is sufficient for RSV replication. Infectious RSV may be produced from the co-transfection of plasmids encoding N, P, L, and M2-1 proteins and the antigenome under control of the T7 promoter into BHK-21 cells that stably express T7 RNA polymerase (BSR cells). Currently research labs typically use a RSV antigenomic cDNA cloned in the plasmid pBR322 (mid-range copy number, 15-20 copies per *E. coli*). In order to maintain the antigenomic cDNA in this plasmid, the bacteria is grown at 30° C. and low aeration. Nevertheless, plasmid rearrangements and clone loss is frequently experienced.

A fraction of RSV cDNA containing the attachment glycoprotein (G) and fusion (F) genes of the virus was found to be unclonable in pUC-based plasmids (500-700 plasmid copies in *E. coli*). This fragment was cloned in a low copy number (approximately 5 copies per *E. coli*) plasmid called pLG338-30.5. The plasmid pLG338-30 was developed to increase the stability of cloned lentivirus glycoproteins. Cunningham et al., Gene, 1993, 124, 93-98. It is hypothesized that cDNA instability in *E. coli* results from the presence of cryptic *E. coli* transcription promoters within viral glycoprotein sequences. Thus, instability of cDNA in “promoterless” plasmids in bacteria can arise because aberrant proteins are expressed from cryptic promoters, leading to toxicity exacerbated by plasmid copy number.

An antigenomic plasmid was generated containing the RSV strain A2 genome with the strain line 19 F gene in place of the A2 F gene. It had been derived from the antigenome plasmid first disclosed in Collins et al., Proc Natl Acad Sci USA., 1995, 92(25):11563-11567 and U.S. Pat. No. 6,790, 449 hereby incorporated by reference. The antigenome was digested out of the plasmid vector and ligated into the pKBS3 BAC.

GalK recombineering reagents were obtained from the NCI and successfully established a BAC-RSV reverse genetics protocol (FIGS. 1 and 2). See http://web.ncifcrf-.gov/research/brb/recombineeringInformation.aspx, hereby incorporated by reference. Mutation of RSV cDNA via BAC recombineering has enhanced the ability to manipulate RSV for generation of mutants. An added benefit of the system is enhanced stability of the full-length antigenomic cDNA in the BAC vector.

The BAC-based RSV antigenome vector was propagated at 32° C. and 250 RPM without observing any vector rearrangements or clone loss in *E. coli*. Thus, BAC-RSV not only enables manipulations via recombineering but also facilitates RSV reverse genetics in general owing to elimination of cDNA instability.

Example 2: RSV Antigenome in BAC Vector (pSynkRSV Line 19 F Construction)

The RSV-BAC pSynkRSV line 19 F contains the modified katushka gene (mKate2, fluorescent protein), and restriction sites for more convenient cloning. To build pSynkRSV, three nucleic acid pieces were synthesized by Gene Art, a German company that synthesizes DNA. These three pieces then have to be put together in the bacterial artificial chromosome (BAC). The three pieces are designated pSynkRSV-BstBI SacI (#1) (SEQ ID NO: 1), pSynkRSV-SacI_ClaI (#2) (SEQ ID NO: 2), and pSynkRSV-ClaI_MluI (#3) (SEQ ID NO: 3). One uses the plasmid pKBS3 as the backbone for constructing pSynkRSV. See FIGS. 3A-E. pSynkRSV contains the bacterial artificial chromosome sequences needed to regulate copy number and partitioning in the bacteria.

To insert the three synthesized segments, one puts oligonucleotide adapters into pKBS3 between two existing restriction enzyme cut sites, BstBI and MluI.

(SEQ ID NO: 4)
CGAATTGGGAGCTCTTTTATCGATGTTGCCTAGGTTTTA (SEQ ID NO: 5)
TTAACCCTCGAGAAAATAGCTACAACGGATCCAAAATGCGC

The overhangs were designed such that the adapter would ligate into pKBS3 at the BstBI and MluI sites. Bold sequences indicate restriction sites: SacI, ClaI, and AvrII from right to left respectively. This produces a multi-cloning site containing the restriction sites BstBI, SacI, ClaI, AvrII, and MluI, in that order, and a plasmid termed pKBS5. See FIG. 3A. One cuts and ligates the SacI_ClaI segment (#2) from Gene Art into pKBS5. See FIG. 3B. Next one cuts and ligates the #3 segment using the enzymes AvrII and MluI (cannot use ClaI again due to an inactive ClaI restriction site in pSynkRSV-ClaI_MluI). See FIG. 3C. At this point, the plasmid pKBS5 contains the Gene Art sequences from SacI to ClaI, some intervening nucleotides (less than 10), and the Gene Art sequences from AvrII to MluI. One cuts and ligates the #1 segment using BstBI and SacI. See FIG. 3D. This RSV BAC contains about 10 unwanted nucleotides between two ClaI sites (that from segment #2 and segment #3). Recombineering is used to delete those nucleotides, thus generating pSynkRSV line 19 F (SEQ ID NO: 6). See FIG. 3E. The three segments should be ligated in this order to avoid potential interference from multiple restriction sites.

The invention claimed is:

1. A nucleic acid comprising SEQ ID NO: 4.
2. A nucleic acid comprising SEQ ID NO: 5.
3. A nucleic acid comprising SEQ ID NO: 4 and SEQ ID NO: 5.
4. A vector comprising the nucleic acid of claim 3.
5. The vector of claim 4 wherein the vector is a plasmid.
6. A cell comprising a vector of claim 4.
7. A vector comprising a single multi-cloning site comprising the restriction sites BstBI, SacI, ClaI, AvrII, and MluI, in that order.
8. The vector of claim 7 wherein the vector is a plasmid.
9. A cell comprising a vector of claim 7.

* * * * *